United States Patent
Fleming et al.

(10) Patent No.: US 10,490,302 B2
(45) Date of Patent: Nov. 26, 2019

(54) SYSTEMS AND METHODS FOR IMPROVING PATIENT ACCESS TO MEDICAL THERAPIES

(71) Applicant: Medtronic, Inc., Minneapolis, MN (US)

(72) Inventors: Joseph Fleming, North Oaks, MN (US); Michael Brandt, Shoreview, MN (US); David Mackmiller, St. Paul, MN (US); Philia Hiotis, Perroy (CH); Meredith Seaborn, Minneapolis, MN (US); Charles Williams, III, Minneapolis, MN (US); Archana Balasubramanyam, Minneapolis, MN (US)

(73) Assignee: Medtronic, Inc, Minneapolis, MN (US)

( * ) Notice: Subject to any disclaimer, the term of this patent is extended or adjusted under 35 U.S.C. 154(b) by 614 days.

(21) Appl. No.: 14/610,239

(22) Filed: Jan. 30, 2015

(65) Prior Publication Data
US 2015/0213233 A1  Jul. 30, 2015

Related U.S. Application Data

(60) Provisional application No. 61/933,375, filed on Jan. 30, 2014.

(51) Int. Cl.
*G06F 19/00* (2018.01)
*G16H 10/60* (2018.01)
*G16H 10/20* (2018.01)

(52) U.S. Cl.
CPC .............. *G16H 10/60* (2018.01); *G16H 10/20* (2018.01)

(58) Field of Classification Search
USPC ........................................................ 705/2–4
See application file for complete search history.

(56) References Cited

U.S. PATENT DOCUMENTS 5,706,441 A * 1/1998 Lockwood ............. G06Q 30/02
705/2
6,151,581 A * 11/2000 Kraftson ............... G06F 19/327
705/2

(Continued)

OTHER PUBLICATIONS

Kaye, Rachelle, et al. "Barriers and success factors in health information technology: A practitioner's perspective." Journal of Management & Marketing in Healthcare 3.2 (2010): 163-175.*

(Continued)

*Primary Examiner* — Mark Holcomb
(74) *Attorney, Agent, or Firm* — Michelle Shen; Roger Hahn; Hahn & Associates

(57) ABSTRACT

The system and method utilizes a computer system having processors that receive quantitative data from users and generate data to facilitate prioritization and reduction of barriers that prevent patients from receiving medical therapies from a particular healthcare provider in rank order. The processors provide an initial rank order of potential barriers based on calculated correlation coefficient, and determine a subsequent rank order of potential barriers based on the calculated correlation coefficient and other data indicative of the effect of each barrier on the patients. The system and method provides for a systematic, data-driven, and validated process to improve patient access to healthcare providers.

22 Claims, 19 Drawing Sheets

(56) References Cited

U.S. PATENT DOCUMENTS

| | | | |
|---|---|---|---|
| 8,073,731 B1 | 12/2011 | Rajasenan | |
| 8,388,532 B2* | 3/2013 | Morgan | A61B 5/0002 600/301 |
| 8,452,610 B2* | 5/2013 | Lipner | G06Q 10/10 705/2 |
| 8,635,143 B1* | 1/2014 | Shenoy | G06Q 40/00 705/3 |
| 2003/0158749 A1* | 8/2003 | Olchanski | G06Q 10/06 705/2 |
| 2004/0049506 A1* | 3/2004 | Ghouri | G06F 19/326 |
| 2004/0117126 A1* | 6/2004 | Fetterman | G06F 19/3456 702/19 |
| 2005/0086080 A1* | 4/2005 | Stump | G06Q 50/22 705/2 |
| 2005/0197862 A1* | 9/2005 | Paterson | G06Q 30/0201 705/2 |
| 2007/0061166 A1* | 3/2007 | Ramasubramanian | G06F 19/328 705/2 |
| 2007/0250352 A1* | 10/2007 | Tawil | G06Q 10/10 705/4 |
| 2008/0015892 A1* | 1/2008 | Gowdy | G06Q 40/08 705/2 |
| 2008/0065411 A1* | 3/2008 | Keeling | G06Q 10/04 705/2 |
| 2008/0133290 A1* | 6/2008 | Siegrist | G06Q 50/22 705/2 |
| 2008/0288286 A1* | 11/2008 | Noreen | G06Q 50/22 705/2 |
| 2010/0131284 A1* | 5/2010 | Duffy | G06Q 30/02 705/2 |
| 2010/0228567 A1* | 9/2010 | Wulf | G06F 19/3456 705/3 |
| 2011/0112853 A1* | 5/2011 | Tong | G06F 19/328 705/2 |
| 2013/0096937 A1* | 4/2013 | Campbell | G06F 19/32 705/2 |
| 2013/0185108 A1 | 7/2013 | Danece | |
| 2013/0197966 A1 | 8/2013 | Liebman | |
| 2014/0081664 A1* | 3/2014 | Mohlenbrock | G06Q 50/22 705/3 |
| 2014/0136237 A1* | 5/2014 | Anderson | G16H 10/60 705/3 |
| 2014/0244292 A1* | 8/2014 | Rosenberg | G06F 19/324 705/2 |
| 2014/0288971 A1* | 9/2014 | Whibbs | G06Q 50/22 705/3 |
| 2014/0297302 A1* | 10/2014 | Vanier | G06F 19/322 705/2 |
| 2014/0343956 A1* | 11/2014 | Cooney | G06Q 30/0201 705/2 |
| 2015/0073813 A1* | 3/2015 | Hacker | G06Q 50/22 705/2 |
| 2015/0127380 A1* | 5/2015 | Aaron | G06F 19/3456 705/3 |

OTHER PUBLICATIONS

European Search Report for Application No. 15153357.7, dated Feb. 15, 2016.

* cited by examiner

Annual market potential within service area

| | Input | Per million | Notes |
|---|---|---|---|
| Country population | 4,585,000 | | |
| Gross indicated prevalence | 9,558 | 2,085 | |
| Population of service area | 850,000 | | |
| Clinical exclusion | 20% | | |
| Economic exclusion | 3% | | |
| Net indicated prevalence | 1,375 | 1,618 | |
| Life span with condition | 4.5 | | |
| Net indicated incidence | 306 | 359 | |
| Average years on therapy | 7.1 | | |
| New procedures potential | 306 | 359 | |
| Device longevity | 4.0 | | |
| Replacement % | 10.9% | | |
| Replacements potential | 75 | 88 | |
| Total annual potential | 381 | 448 | |

Benchmarking: Comparison points — 100

| Country/region | Procedures/M: |
|---|---|
| Ireland | 85 |
| UK | 84 |
| Western Europe | 82 |
| W. Eur. & Can | 80 |

FIG. 4

| Barrier name | Barrier description | Ability to impact (0-10) | Impact on success (0-10) | Notes | Priority |
|---|---|---|---|---|---|
| 1. Clinical evidence | | | | | ☐ |
| 3. Complication rates | | | | | ☐ |
| 5. Clinical outcomes meas. | | | | | ☐ |
| 7. Budget availability | Limited budgets for CRT | 4 | 9 | | ☐ |
| 8. Cost of care, procedure | | | | | ☐ |
| 12. Financial metrics | | | | | ☐ |
| 13. Diagnostic capacity | | | | | ☐ |
| 17. Proc. standardization | | | | | ☐ |
| 18. Length of stay | | | | | ☐ |
| 21. Patient concentration | | | | | ☐ |

Click to add row

FIG. 10

SYSTEMS AND METHODS FOR IMPROVING PATIENT ACCESS TO MEDICAL THERAPIES

The invention relates generally to methods and systems for identifying barriers that prevent patient access to medical therapies and prioritizing the barriers in rank order. The identified barriers can be specific to a particular healthcare provider impeding patient access wherein a customized rank order of the barriers can be used by a healthcare provider to allocate resources to remove the barriers and result in adoption of the medical therapy. The systems and methods can also provide an action plan to assist healthcare providers in implementing strategies for increasing adoption rates and thereby improve efficiency, increase revenue, and improve patient access to a medical therapy.

BACKGROUND

New advances in clinical technology can result in innovations for heart disease, cancer, renal failure, and other conditions providing substantial benefits for patients including longer life expectancy and improved quality of life. However, the adoption rate of new technologies can sometimes lag behind the introduction of advances in devices, drugs, diagnostics, therapeutic techniques, and surgical equipment. In general, patients sometimes do not access particular medical therapies from particular healthcare providers due to one or more barriers preventing or discouraging patients and providers from accessing a medical therapy from a particular healthcare provider. Although healthcare providers such as hospitals, clinics, physician's offices, outpatient treatment centers, attempt to offer the most advanced, clinical-proven methods for diagnosis and treatment, adoption is oftentimes slow or non-uniform. For example, bare-metal stents prior to 2003 were used by cardiologists seeking to perform revascularization for blockages in the heart. In April of 2003, the FDA approved the use of coated anti-proliferative but more expensive drug-eluting stents, designed to reduce re-narrowing of the artery at the location of the original stent. Adoption was rapid but uneven wherein in the year following their introduction, drug-eluting stents comprised 83% of total stents among Medicare enrollees in the top quintile of hospitals, but just 33% in the low quintile hospitals (See, Adopting Technological Innovation in Hospitals: Who Pays and Who Benefits?, American Hospital Association, October 2006). This adoption disparity suggests that one or more extant barriers to patient access can prevent patients from accessing advanced medical therapies from a particular healthcare provider and result in lowered outcomes for patients and reduced reimbursement to providers.

As such, there is clear need for systems to provide a statistically rigorous method for identifying potential barriers to patient access of a medical therapy. The need extends to providing healthcare providers with analytical tools to empirically analyze identified barriers to result in specific recommendations for reducing barriers to care. There is also a need to increase the frequency with which the healthcare provider provides the medical therapy based on statistical methods.

The need extends to a healthcare provider having a means to reduce barriers to patients accessing the medical therapy from the healthcare provider. The need includes helping identify the barriers that a healthcare provider may optimally invest time, money, and other resources into reducing the identified barriers. Because the healthcare provider may only have a finite amount of time, money, and resources to invest in reducing identified barriers, the need includes prioritizing which of the barriers to address first. Because the healthcare provider may have determined that barriers exist to patients accessing multiple different types of medical therapy from the healthcare provider, the need also includes prioritizing the medical therapies.

There is also a need for methods implementing the steps of the described systems. The methods should provide steps for obtaining a reproducible framework for analyzing barriers to medical therapy using specially adapted computer technologies. The need for such methods extends to providing outputs that can be used to inform or provide useful recommendations to healthcare provider on how to reduce barriers to patient access.

The need also includes methods and systems that provide analytical tools for estimating a market opportunity for a particular healthcare provider and using the estimates in a barrier analysis resulting in improved patient access to a medical therapy. The need further includes improving the adoption of medical therapy by allowing users to design and execute a strategy to improve adoption rates. The need also includes methods and systems for implementing statistical tools to determine a specific healthcare provider's action plan to improve adoption rates.

SUMMARY

This disclosure describes techniques for generating data to facilitate a process of increasing patient access to healthcare services provided by a healthcare provider. In the first aspect of the invention, a computing system can receive quantitative data from one or more users. In any embodiment of the first aspect of the invention, the computing system may generate data targeted to facilitating a decision-making process regarding reduction of one or more barriers to patients receiving a medical therapy from the healthcare provider. In any embodiment of the first aspect of the invention, the computing system may receive opportunity sizing input data and may determine, based on the opportunity sizing input data, opportunity sizing output data. The opportunity sizing output data may provide quantitative information regarding potential opportunities for the healthcare provider to provide a medical therapy to members of a patient population. In any embodiment of the first aspect of the invention, the computing system may receive barrier assessment input data and may determine, based on the barrier assessment input data, quantitative data indicative of effects of a plurality of potential barriers to members of the patient population obtaining the medical therapy from the healthcare provider. In any embodiment of the first aspect of the invention, the computing system may also receive quantitative barrier prioritization input data and may determine, based on the quantitative barrier prioritization data, quantitative data indicative of which of the plurality of potential barriers to prioritize for reduction.

The second aspect of the invention relates to a method comprising: outputting, by a computing system, for display, a plurality of multiple-choice questions related to a plurality of barriers to patients receiving a medical therapy from a healthcare provider, wherein the plurality of barriers include barriers related to: clinical evidence, reimbursement, physician economics, physician capacity and training level for the medical therapy, and treatment capacity; receiving, by the computing system, indications of user input indicating selected answers to the multiple-choice questions, wherein each of the answers to the multiple-choice questions corresponds to a quantitative value; and generating, by the computing system and based on the quantitative values corresponding to the selected answers, one or more diagrams indicating relative severity of the barriers in preventing the patients from receiving the medical therapy from the healthcare provider.

The third aspect of the invention relates to a computing system comprising a data storage system storing computer-executable instructions and one or more processors configured to execute the instructions, execution of the instructions configuring the computing system to: output, for display, a plurality of multiple-choice questions related to a plurality of barriers to patients receiving a medical therapy from a healthcare provider, wherein the plurality of barriers include barriers related to: clinical evidence, reimbursement, physician economics, physician capacity and training level for the medical therapy, and treatment capacity; receive indications of user input indicating selected answers to the multiple-choice questions, wherein each of the answers to the multiple-choice questions corresponds to a quantitative value; and generate, based on the quantitative values corresponding to the selected answers, one or more diagrams indicating relative severity of the barriers in preventing the patients from receiving the medical therapy from the healthcare provider.

The fourth aspect of the invention relates to a non-transitory computer-readable data storage medium having instructions stored thereon that when executed configure a computing system to: output, for display, a plurality of multiple-choice questions related to a plurality of barriers to patients receiving a medical therapy from a healthcare provider, wherein the plurality of barriers include barriers related to: clinical evidence, reimbursement, physician economics, physician capacity and training level for the medical therapy, and treatment capacity; receive indications of user input indicating selected answers to the multiple-choice questions, wherein each of the answers to the multiple-choice questions corresponds to a quantitative value; and generate, based on the quantitative values corresponding to the selected answers, one or more diagrams indicating relative severity of the barriers in preventing the patients from receiving the medical therapy from the healthcare provider.

The fifth aspect of the invention relates to a computing system comprising means for outputting, for display, a plurality of multiple-choice questions related to a plurality of barriers to patients receiving a medical therapy from a healthcare provider, wherein the plurality of barriers include barriers related to: clinical evidence, reimbursement, physician economics, physician capacity and training level for the medical therapy, and treatment capacity; means for receiving, indications of user input indicating selected answers to the multiple-choice questions, wherein each of the answers to the multiple-choice questions corresponds to a quantitative value; and means for generating, based on the quantitative values corresponding to the selected answers, one or more diagrams indicating relative severity of the barriers in preventing the patients from receiving the medical therapy from the healthcare provider.

The sixth aspect of the invention relates to a system that can comprise one or more processors configured to provide an initial barrier prioritization rank order of one or more barriers wherein the initial barrier prioritization rank order is based on a correlation coefficient calculated for each of the one or more barriers. The one or more processors can be configured to receive data indicative of the one or more barriers preventing patients from receiving a medical therapy from a healthcare provide, and the one or more processors can be configured to determine a subsequent barrier prioritization rank order using the initial barrier prioritization rank order based on the received data indicative of the one or more barriers preventing patients from receiving a medical therapy from a healthcare provider.

In any embodiment of the sixth aspect of the invention, the correlation coefficient can be calculated for each barrier with respect to an annual adoption rate.

In any embodiment of the sixth aspect of the invention, the data indicative of the one or more barriers preventing patients from receiving a medical therapy from a healthcare provider can be obtained from a scaled response to a multiple choice question, wherein the scaled response is used to determine the subsequent barrier prioritization rank order.

In any embodiment of the sixth aspect of the invention, the one or more processors can be configured to determine a barrier prioritization matrix based on an indication of priority of the barriers listed in the subsequent barrier prioritization rank order.

In any embodiment of the sixth aspect of the invention, the one or more barriers can be selected from the group consisting of: Clinical Evidence, Practice Guidelines, Complication Rates, Readmissions, Clinical Outcomes Measurement, Reimbursement, Budget Availability, Cost of Care for Procedure, Cost of Care Follow-up, Physician Economics, Infrastructure Investment, Financial Metrics, Diagnostic Capacity, Patient Screening Selection, Treatment Capacity, Clinician Capacity in Skill, Procedure Standardization, Length of Stay, Follow-up Capacity, Follow-up Care Process, Patient Concentration, Referrer Motivation, Community Referral Links, Interdepartment Patient Pathways, Prescriber Motivation, Standardization of Care, Hospital Reputation, Patient Education and Resources, Patient Experience Measurement, and Patient Satisfaction.

In any embodiment of the sixth aspect of the invention, the barriers can be grouped in categories of any one or more of Clinical Excellence, Hospital Economics, Capacity and Efficiency, Patient Pathways, and Patient Experience.

In any embodiment of the sixth aspect of the invention, the one or more processors can provide any one of the any one of the initial barrier prioritization rank order, subsequent barrier prioritization rank order, a barrier prioritization matrix, or an action plan.

In any embodiment of the sixth aspect of the invention, the system can comprise a graphical user interface configured to display one or more multiple choice questions regarding the one or more barriers, and wherein the data indicative of one or more barriers to patients receiving a medical therapy from a healthcare provider is obtained at least in part from one or more answers to the multiple choice questions.

In any embodiment of the sixth aspect of the invention, at least part of the data indicative of one or more barriers to patients receiving a medical therapy from a healthcare provider can be obtained electronically by the system.

In any embodiment of the sixth aspect of the invention, the one or more processors can provide a barrier prioritization matrix based on an indication of priority and the subsequent barrier prioritization rank order wherein the impact on success is determined as a function the ability to impact.

In any embodiment of the sixth aspect of the invention, the system can be configured to output an action planning interface for display; wherein the action planning interface displays a prioritization of actions; wherein the prioritization of actions is based on the estimated effect of an action on reducing a barrier and the estimated effect of reducing the barrier on the number of times the health care provider provides the medical therapy.

The seventh aspect of the invention is directed to determining an initial barrier prioritization rank order of one or more barriers, receiving data indicative of the one or more barriers preventing patients from receiving a medical therapy from a healthcare provider, calculating a relative severity between each one of the one or more barriers using a weight for each of the barriers, the weight being obtained from the correlation coefficient, and determining a subsequent barrier prioritization rank order using the initial barrier prioritization rank order based on the received data indicative of the one or more barriers preventing patients from receiving a medical therapy from a healthcare provider.

In any embodiment of the seventh aspect of the invention, the weights for the initial barrier prioritization rank order can be based on a correlation coefficient calculated for each of the one or more barriers.

In any embodiment of the seventh aspect of the invention, the data indicative of the one or more barriers preventing patients from receiving a medical therapy from a healthcare provider can be obtained from a scaled response to a multiple choice question, wherein the scaled response is used to determine the subsequent barrier prioritization rank order.

In any embodiment of the seventh aspect of the invention, the method can comprise indicating priority for one or more barriers in the subsequent barrier prioritization rank order.

In any embodiment of the seventh aspect of the invention, the method can include estimating an ability of the health care provider to reduce one or more of the barriers.

In any embodiment of the seventh aspect of the invention, the estimation of the ability of the health care provider to reduce one or more of the barriers can be based at least in part on a degree of success in reducing the barriers in one or more other therapies by the healthcare provider.

In any embodiment of the seventh aspect of the invention, the method can further comprise determining an action plan, wherein the action plan provides one or more actions that the healthcare provider can take in order to reduce one or more of the barriers to patients receiving the medical therapy from the healthcare provider.

In any embodiment of the seventh aspect of the invention, the actions can be prioritized based on an estimated effect of taking an action on the number of times the healthcare provider will provide the medical therapy in the future.

In any embodiment of the seventh aspect of the invention, the method can comprise displaying any one of the initial barrier prioritization rank order, subsequent barrier prioritization rank order, a barrier prioritization matrix, or an action plan.

The details of one or more examples of the techniques are set forth in the accompanying drawings and the description below. Other features, objects, and advantages of the techniques will be apparent from the description, drawings, and claims.

BRIEF DESCRIPTION OF DRAWINGS

FIG. 4 is a conceptual diagram illustrating a first portion of an example opportunity sizing interface, in accordance with one or more techniques of this disclosure.

FIG. 10 is a conceptual diagram showing an example barrier prioritization interface, in accordance with one or more techniques of this disclosure.

DETAILED DESCRIPTION

Figure 1:
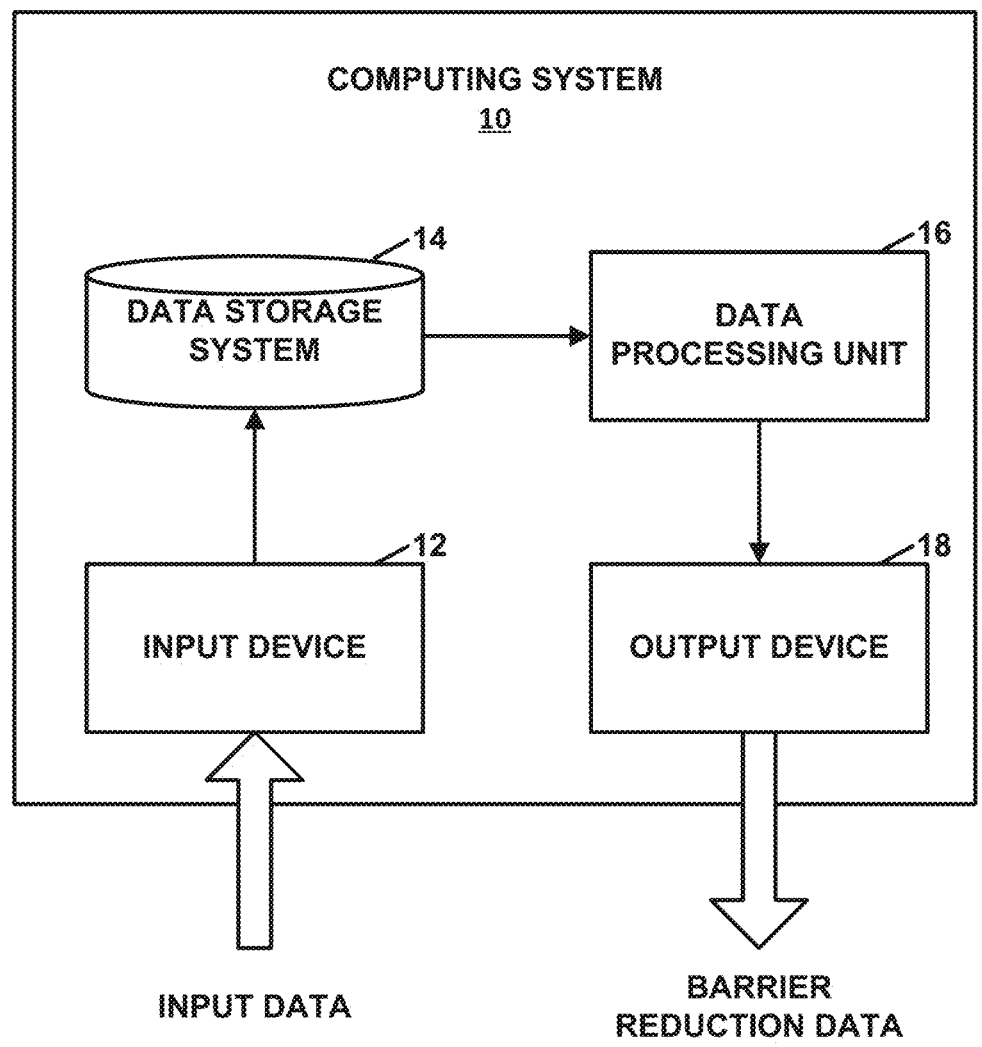
FIG. 1 illustrates an example computing system for generating data targeted to facilitating a decision-making process regarding reduction of one or more barriers to patients receiving a medical therapy from a healthcare provider, in accordance with one or more techniques of this disclosure.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

"Ability to impact" can refer to the ability of a healthcare provide to reduce one or more barriers to patients receiving a medical therapy from the healthcare provider. The term can be a translated into numerical form for quantification by any means known to those of ordinary skill.

An "action planning interface," or an "action plan" refers to one or more specific processes that can be carried out to reduce one or more barriers to a patient receiving therapy from a healthcare provider.

"Annual adoption rate" can refer to a measure of the rate at which a medical therapy is used. The annual adoption rate can be expressed as number of times a therapy is provided divided by the number of years the therapy has been available, times 1+the penetration of incidence.

"Barrier prioritization" can refer to an order of barriers to patients receiving a medical therapy in an order indicative of the relative effect each of the barriers currently has on the number of patients receiving the medical therapy.

"Barrier prioritization matrix" can refer to a graph of one or more barriers, and can include a graph wherein a barrier of an impact of success is a function of a barrier of an ability to impact.

"Barriers to patients receiving a medical therapy" can refer to any one or more factor that tends to cause patients not to receive a medical therapy from a healthcare provider.

"Budget availability: can refer to the amount of money a healthcare provider can allocate toward a medical therapy. The term can be a translated into numerical form for quantification by any means known to those of ordinary skill.

"Capacity and efficiency" can refer to barriers associated with the ability of a healthcare provider to provide a medical therapy, including the ability to provide for diagnostic and follow-up care relating to the medical therapy.

"Clinical evidence" can refer to data showing patient outcomes. The term can be a translated into numerical form for quantification by any means known to those of ordinary skill.

"Clinical excellence" can refer to potential barriers relating to the quality of a medical therapy or a healthcare provider providing the medical therapy, and the ability of a healthcare provider to measure and improve the medical therapy outcomes.

"Clinical outcomes measurement" can refer to whether the result of a medical therapy can be or is measured. The term can be a translated into numerical form for quantification by any means known to those of ordinary skill.

"Clinician capacity in skill" can refer to the level of training and experience of clinicians in providing a medical therapy. The term can be a translated into numerical form for quantification by any means known to those of ordinary skill.

"Community referral links" can refer to the likeliness of referring physicians referring potential patients to a particular healthcare provider for a medical therapy. The term can be a translated into numerical form for quantification by any means known to those of ordinary skill.

"Complication rates" can refer to the frequency that a medical therapy will result in adverse effects to the patient. The term can be a translated into numerical form for quantification by any means known to those of ordinary skill.

The term "comprising" can include, but is not limited to, whatever follows the word "comprising." Thus, use of the term indicates that the listed elements are required or mandatory but that other elements are optional and may or may not be present.

The term "configured to display" refers to the ability of a device to generate a particular visual output.

The term "configured to receive" refers to the ability of a device to obtain data from another source. The device can be configured to receive data via electronic transmission of the data including wireless transmission or by manual entry of the data.

The term "consisting of" can include and is limited to whatever follows the phrase "consisting of." Thus, the phrase indicates that the limited elements are required or mandatory and that no other elements may be present.

The term "consisting essentially of" can include whatever follows the term "consisting essentially of" and additional elements, structures, acts or features that do not affect the basic operation of the apparatus, structure or method described.

A "correlation coefficient" can be a measure of the strength and direction of a linear relationship between two random variables. In one form, the correlation coefficient can be obtained from the covariance of two random variables divided by the product of the standard deviations of the two random variables.

"Cost of care for follow-up" can refer to the ongoing cost of a medical therapy after the therapy is performed due to routine follow-up care. The term can be a translated into numerical form for quantification by any means known to those of ordinary skill.

"Cost of care for a procedure" can refer to the cost of obtaining a medical therapy in relation to the cost to a patient of not receiving the medical therapy. The term can be a translated into numerical form for quantification by any means known to those of ordinary skill.

The term "data indicative of" can refer to any information that tends to show the state of a variable. For example, data indicative of a barrier to a patient receiving a medical therapy can refer to any information that tends to show the existence of or severity of the barrier.

"Diagnostic capacity" can refer to the ability of a healthcare provider to diagnose potential patients for a medical therapy. The term can be a translated into numerical form for quantification by any means known to those of ordinary skill.

"Electronically receiving" refers to a system receiving data in electronic form. The data can be received through wireless or wired electronic communication. In any embodiment, the system can automatically update internal data based on new data received electronically.

"Electronic records" are electronic versions of data concerning past or present events.

The term "estimated effect" refers to the likely effect of changing a variable on an outcome. For example, the estimated effect of reducing a barrier can refer to the likely change in the number of times a healthcare provider provides a medical therapy as a result of reducing the barrier.

"Executional milestones" can refer to identifiable benchmarks in a larger process.

"Financial metrics" can refer to the ability of a healthcare provider to track or measure the finances associated with a medical therapy. The term can be a translated into numerical form for quantification by any means known to those of ordinary skill.

"Follow-up capacity" can refer to the ability of a healthcare provider to provide the necessary equipment, physicians, nurses and infrastructure to carry out expected follow-up procedures due to a patient receiving a medical therapy.

The term can be a translated into numerical form for quantification by any means known to those of ordinary skill.

"Follow-up care process" can refer to the degree to which follow-up care is standardized and the degree to which physicians providing treatment and physicians providing follow up care are linked. The term can be a translated into numerical form for quantification by any means known to those of ordinary skill.

A "graphical user interface" can be a type of computer interface that allows users to interact with an electronic device through graphical icons and visual indicators.

A "healthcare provider" can be any hospital, doctor or treatment facility that provides medical therapy to patients.

"Hospital economics" can refer to potential barriers associated with the costs of providing a medical therapy and the ability of a healthcare provider to be reimbursed for a medical therapy.

"Hospital reputation" can refer to the perceived quality of a healthcare provider as compared to other healthcare providers. The term can be a translated into numerical form for quantification by any means known to those of ordinary skill.

An "impact on success" can refer to the effect on the number of times a healthcare provider provides a therapy due to reduction of one or more barriers.

An "initial barrier prioritization rank order" can refer to an order of potential barriers ranked based on calculated correlation coefficients.

"Infrastructure investment" can refer to the capital investment needed to perform a medical therapy, including but not limited to, diagnostic investment, medical devices, or surgical equipment. The term can be translated into numerical form for quantification by any means known to those of ordinary skill.

"Interdepartmental patient pathways" can refer to the degree to which care associated with a medical therapy is standardized across different departments of a healthcare provider. The term can be a translated into numerical form for quantification by any means known to those of ordinary skill.

"Length of stay" can refer to the amount of time a patient is expected to remain in a healthcare facility after receiving the medical treatment. The term can be a translated into numerical form for quantification by any means known to those of ordinary skill.

The term "medical therapy" refers to any surgical or non-surgical method of treating patients with a particular medical condition. The term can be a translated into numerical form for quantification by any means known to those of ordinary skill.

"Multiple choice questions" are questions in which a list of options of potential answers is provided to the question.

"Patient concentration" can refer to the degree to which potential patients for a medical procedure are in the care of a prescribing physician. The term can be a translated into numerical form for quantification by any means known to those of ordinary skill.

"Patient education and resources" can refer to the ability of potential patients to learn about a medical therapy, and the available support for patients that undergo the medical therapy. The term can be a translated into numerical form for quantification by any means known to those of ordinary skill.

"Patient experience" can refer to barriers associated with the level of care, education, and support provided to patients undergoing a medical therapy from a healthcare provider.

"Patient experience measurement" can refer to the ability of a healthcare provider to measure and track the experience of patients undergoing a medical procedure, and the ability of a healthcare provider to improve the medical therapy based on the patient experiences. The term can be a translated into numerical form for quantification by any means known to those of ordinary skill.

"Patient pathways" can refer to barriers associated with the ability to have individual patients seek a medical therapy from a healthcare provider.

"Patient satisfaction" can refer to the subjective satisfaction of a patient that has undergone a medical procedure and whether the staff of a healthcare provider is motivated to improve the subjective satisfaction of patients. The term can be a translated into numerical form for quantification by any means known to those of ordinary skill.

"Patient screening and selection" can refer to the ability of a healthcare provider to identify potential patients for a medical therapy. The term can be a translated into numerical form for quantification by any means known to those of ordinary skill.

"Physician capacity" can refer to the possible number of times that of a physician or healthcare provider to provide a medical therapy in a given time period. The term can be a translated into numerical form for quantification by any means known to those of ordinary skill.

"Physician economics" can refer to the expected reimbursement to a healthcare provider for providing a medical therapy relative to the cost to the healthcare provider of providing the medical therapy. The term can be a translated into numerical form for quantification by any means known to those of ordinary skill.

"Practice guidelines" can refer to whether a particular therapy is generally recommended for a particular medical condition. The term can be a translated into numerical form for quantification by any means known to those of ordinary skill.

"Prescriber motivation" can refer to the degree to which prescribing physicians are aware of a medical therapy, and the likelihood that prescribing physicians will prescribe the medical therapy for potential patients. The term can be a translated into numerical form for quantification by any means known to those of ordinary skill.

"Prioritization of actions" can refer to a list of possible actions in an order corresponding to the estimated effect each of the actions. For example, prioritization can be determined based on the number of times a healthcare provider provides a medical therapy.

"Procedure standardization" can refer to the degree of variability in pre-operative and operative procedures associated with a medical therapy among healthcare providers. The term can be a translated into numerical form for quantification by any means known to those of ordinary skill.

The term "processor" as used herein is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "prioritize" refers to the process of determining the order of steps that should be taken.

"Readmissions" can refer to the frequency with which patients that have undergone a particular medical therapy require additional therapy for the same medical problem. The term can be a translated into numerical form for quantification by any means known to those of ordinary skill.

"Referrer motivation" can refer to the degree to which physicians with potential patients for a medical treatment are aware of a healthcare provider providing the medical therapy, and how likely the physicians are to direct patients to the healthcare provider for the medical therapy. The term can be a translated into numerical form for quantification by any means known to those of ordinary skill.

"Reimbursement" can refer to the ability of a healthcare provider or a patient to receive at least a portion of the cost of a medical therapy from a third party. The term can be a translated into numerical form for quantification by any means known to those of ordinary skill.

The term "relative severity" refers to the effect of a first barrier to patients receiving a medical therapy as compared to the effect of a second barrier to patients receiving a medical therapy.

A "scaled response" refers to a response to a multiple choice question, wherein the response is converted into a quantitative value.

"Service area" refers to a geographical area and can be a translated into numerical form for quantification by any means known to those of ordinary skill.

"Standardization of care" can refer to the degree of variability in care across departments for a medical therapy. The term can be a translated into numerical form for quantification by any means known to those of ordinary skill.

A "subsequent barrier prioritization rank order" can refer to an order of potential barriers ranked based on calculated correlation coefficients and other data indicative of the effect of each barrier on patients receiving a medical therapy from a healthcare provider.

"Training level" refers to the degree of expertise and quantity or quality of training. The training can refer to physician expertise in providing a specific medical therapy and can be a translated into numerical form for quantification by any means known to those of ordinary skill.

"Treatment capacity" can refer to the number of times a healthcare provider can provide a medical therapy. The term can be based on the physical constraints of the healthcare provider facility and the number of physicians available to provide the medical therapy. The term can be a translated into numerical form for quantification by any means known to those of ordinary skill.

"User inputted variables" can be variables that are obtained by a user of a system, as opposed to variables automatically obtained from external sources.

The term "weight" can refer to a factor by which a variable can be scaled in order to show the estimated effect of changing the variable on an outcome.

Barrier Identification System

This disclosure describes computer-implemented techniques for reducing barriers to patients receiving a medical therapy from a healthcare provider. As mentioned briefly above, there may be a variety of reasons why patients who have a medical condition treatable by a medical therapy do not receive the medical therapy from a healthcare provider. In other words, there may be a variety of barriers to patients receiving the medical therapy from the healthcare provider. These reasons may include geographic reasons, such as lack of transportation, or economic reasons, such as lack of health insurance. Other reasons may include underdeveloped networks of physicians to refer patients to the healthcare provider for the medical therapy, lack of trained personnel to perform the medical therapy additional times, and so on.

As indicated above, this disclosure describes computer-implemented techniques for reducing barriers to patients receiving a medical therapy from a healthcare provider. As described herein, a computing system may receive quantitative data and generate, based on the quantitative data, data targeted to facilitating a decision-making process regarding reduction of one or more barriers to patients receiving a medical therapy from a healthcare provider. For instance, in any embodiment of the first through seventh aspects of the invention, the computing system may output, for display, a plurality of multiple-choice questions related to a plurality of barriers to patients receiving a medical therapy from a healthcare provider. The plurality of barriers may include barriers related to: clinical evidence, reimbursements, physician economics, physician capacity and training level for the medical therapy, treatment capacity, and so on. Furthermore, in any embodiment of the first through seventh aspects of the invention, the computing system may receive indications of user input indicating selected answers to the multiple-choice questions. Each of the answers to the multiple-choice questions may correspond to a quantitative value. The computing system may generate, based on the quantitative values corresponding to the selected answers, one or more diagrams indicating relative severity of the barriers in preventing the patients from receiving the medical therapy from the healthcare provider.

In any embodiment of the first through seventh aspects of the invention, the computing system may generate opportunity sizing data that quantify the size of an opportunity for the healthcare provider to provide the medical therapy to patients. Furthermore, in any embodiment of the first through seventh aspects of the invention, the computing system may generate barrier assessment data that quantify effects of particular barriers to patients receiving the medical therapy from the healthcare provider. Moreover, in any embodiment of the first through seventh aspects of the invention, the computing system may generate quantitative barrier prioritization data targeted to prioritization of one or more of the barriers.

The attached drawings illustrate examples. Elements indicated by reference numbers in the attached drawings correspond to elements indicated by like reference numbers in the following description. In the attached drawings, stacked elements may indicate the presence of one or more similar elements. In this disclosure, elements having names that start with ordinal words (e.g., "first," "second," "third," and so on) do not necessarily imply that the elements have a particular order. Rather, such ordinal words may merely be used to refer to different elements of a same or similar type. It will be understood that various examples of this disclosure may be used together or separately.

FIG. 1 illustrates an example computing system 10 for generating data targeted to facilitating a decision-making process regarding reduction of one or more barriers to patients receiving a medical therapy from a healthcare provider, in accordance with any embodiment of the first through seventh aspects of the invention. Computing system 10 may be implemented in various ways. In any embodiment of the first through seventh aspects of the invention, computing system 10 may comprise one or more computing devices, such as one or more desktop computers, laptop computers, tablet computers, smartphones, server computing devices, mainframe computers, and other types of computing devices.

In the example of FIG. 1, computing system 10 comprises an input device 12, a data storage system 14, a data processing unit 16, and an output device 18. In any embodiment of the first through seventh aspects of the invention, the techniques may be implemented using a computing system that does not include one or more of an input device, a data storage unit, a data processing unit, or an output device. Furthermore, in any embodiment of the first through seventh aspects of the invention, input device 12, data storage system 14, data processing unit 16, and/or output device 18 may be implemented on two or more physically separate devices.

Input device 12 may comprise a device configured to receive input. In any embodiment of the first through seventh aspects of the invention, input device 12 comprises a device configured to receive user input (i.e., input provided by a human user). For instance, input device 12 may comprise a keyboard, a mouse, a touch- or presence-sensitive screen, a keypad, or another type of device configured to receive user input. Furthermore, in any embodiment of the first through seventh aspects of the invention, input device 12 comprises a device configured to receive input from one or more other computing devices. For instance, input device 12 may comprise interface hardware for wired or wireless communication with one or more other computing devices.

Data storage system 14 may comprise one or more devices configured to store data. In any embodiment of the first through seventh aspects of the invention, data storage system 14 comprises one or more random access memory (RAM) modules, flash memory units, hard disk drives, cache memory units, and/or other types of devices configured to store data. Other devices, systems, or components may be able to read data stored data storage system 14. Hence, data storage system 14 may be referred to herein as comprising one or more computer-readable data storage media.

Data processing unit 16 may comprise one or more devices configured to process data. Processing data may comprise receiving data and generating new data based on the received data. In this disclosure, the phrase "based on" may indicate "based at least in part on." In any embodiment of the first through seventh aspects of the invention, data processing unit 16 may comprise one or more microprocessors, application-specific integrated circuits, signal processors, and/or other types of devices configured to process data. In any embodiment of the first through seventh aspects of the invention, data processing unit 16 may perform particular actions, including particular actions implementing techniques of this disclosure, by executing computer-executable instructions. In any embodiment of the first through seventh aspects of the invention, data processing unit 16 may perform actions associated with some techniques of this disclosure by executing instructions of a spreadsheet application. Such computer-executable instructions may be stored in data storage medium and/or one or more other computer-readable data storage media (e.g., non-transitory computer-readable data storage media).

Output device 18 may comprise one or more devices configured to output data. In any embodiment of the first through seventh aspects of the invention, output device 18 comprises a device configured to output data for human consumption. For instance, output device 18 may comprise a video screen, speaker, touchscreen, monitor, or other type of device configured to output data for human consumption. Furthermore, in any embodiment of the first through seventh aspects of the invention, output device 18 comprises a device configured to receive input from one or more other computing devices. For instance, output device 18 may comprise interface hardware for wired or wireless communication with one or more other computing devices.

Computing system 10 may implement techniques for reducing barriers to patients receiving a medical therapy from a healthcare provider. In any embodiment of the first through seventh aspects of the invention, the healthcare provider owns and/or operates computing system 10. In any embodiment of the first through seventh aspects of the invention, another party, such as an entity providing consulting services owns and/or operates computing system 10. Furthermore, in any embodiment of the first through seventh aspects of the invention, computing system 10 comprises a cloud-based computing system used by the healthcare provider and/or other parties.

The healthcare provider may comprise an entity that provides medical therapies to patients. The healthcare provider may comprise various types of entities. For instance, the healthcare provider may comprise one or more corporations, companies, foundations, trusts, non-profit organizations, non-governmental organizations, governmental organizations, and/or other types of entities. In some instances, the healthcare provider may comprise one or more hospitals, clinics, physicians' offices, outpatient care centers, and other types of facilities for providing healthcare to patients. Many examples of this disclosure assume that the healthcare provider comprises a hospital. However, the techniques of this disclosure are not limited to hospitals and such examples may be understood to apply to other healthcare facilities or entities.

The healthcare provider may provide various types of medical therapies to patients. Example types of medical therapies may include medical devices, surgical procedures, physical therapies, occupational therapies, consulting services, surgical therapies, internal medicine therapies, psychiatric therapies, dental or orthodontic therapies, pharmaceutical therapies, cancer therapies, and other types of therapies for the treatment of medical conditions. Many examples of this disclosure assume that the medical therapy involves a medical device. However, the techniques of this disclosure are not limited to medical devices and such examples may be understood to apply to other types of medical therapies.

In some instances, the healthcare provider may be capable of providing a medical therapy to more patients than the healthcare provider is currently doing. For example, the medical therapy may comprise a particular implantable cardiac defibrillator that treats atrial fibrillation. In this example, statistical surveys of atrial fibrillation may suggest that there is a need in the population served by the healthcare provider to perform approximately 500 implantations of the particular implantable cardiac defibrillator per year. Furthermore, in this example, the healthcare provider may only be performing 100 implantations of the particular implantable cardiac defibrillator per year. Hence, in this example, the healthcare provider may be able to implant more of units of the particular implantable cardiac defibrillator than healthcare provider is currently doing.

There may be a variety of reasons why the healthcare provider is providing the medical therapy less frequently than the healthcare provider is capable of doing. In other words, there may be one or more barriers to patients accessing the medical therapy from the healthcare provider. For example, the healthcare provider may have a poor reputation that discourages patients from wanting to obtain the medical therapy from the healthcare provider. In another example, the healthcare provider may rely on a network of physicians to refer patients to the healthcare provider for the medical therapy. In this example, if physicians in the network of physicians are not adequately aware of the healthcare provider's capabilities for providing the medical therapy, the healthcare provider may not have the opportunity to provide the medical therapy to as many patients.

In accordance with one or more techniques of this disclosure, computing system 10 may receive data and may generate, based on the received data, data targeted to facilitating a decision-making process regarding reduction of one or more barriers to patients receiving a medical therapy from a healthcare provider. For instance, in the example of FIG. 1, input device 12 of computing system 10 may receive input data. Data storage system 14 may store the input data and/or data generated based on the input data. Data processing unit 16 may process data stored in data storage system 14 to generate data targeted to facilitating the decision-making process regarding reduction of one or more barriers to patients receiving the medical therapy from the healthcare provider. Output device 18 may output the data targeted to facilitating the decision-making process regarding reduction of one or more barriers to patients receiving the medical therapy from the healthcare provider.

As described herein, the techniques of this disclosure may provide for a systematic, data-driven and validated process to improve patient access to healthcare providers (e.g. hospitals). The techniques of this disclosure may provide healthcare providers with tools and collaborative insights to optimize patient access by quantifying patient treatment needs in a service area of the healthcare provider, identifying area of under- and over-treatment, introducing performance metrics, understanding barriers to patient access, informing strategies to overcome barriers, and aligning organizations around key barriers, objectives and strategies.

Figure 2:
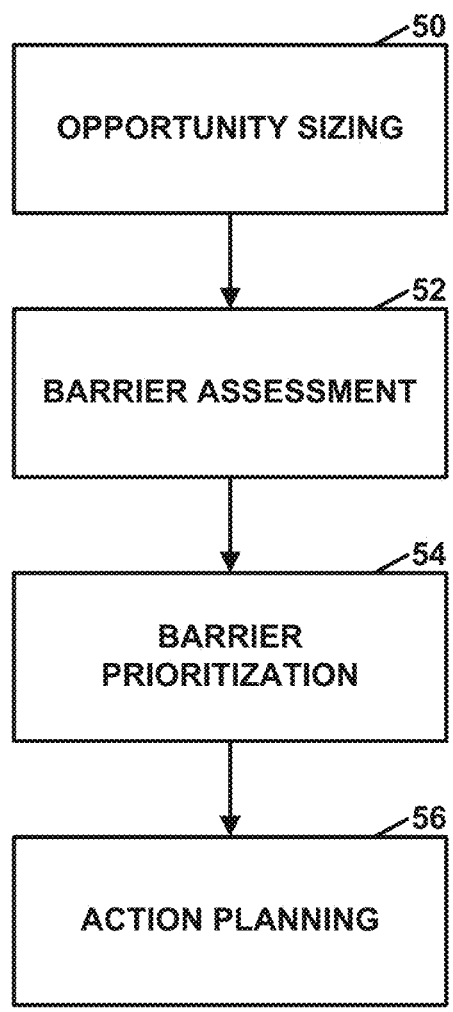
FIG. 2 is a flowchart illustrating an example operation for improving access to a medical therapy provided by a healthcare facility, in accordance with one or more techniques of this disclosure.

FIG. 2 is a flowchart illustrating an example decision-making process facilitated by computing system 10, in accordance with one or more techniques of this disclosure. Generally, a committee of stakeholders associated with the healthcare provider performs some or all of the decision-making process of FIG. 2. Furthermore, the committee generally performs the decision-making process of FIG. 2 with the assistance of one or more consultants who use computing system 10 to facilitate the decision-making process. In any embodiment of the first through seventh aspects of the invention the decision making process can be made by any individual or group and need not be a committee.

In the example of FIG. 2, a healthcare provider may first perform an opportunity sizing process (50). In other words, the healthcare provider may perform a process to quantify a treatment need. Next, the healthcare provider may perform a barrier assessment process (52). The healthcare provider may then perform a barrier prioritization process (54). The healthcare provider may then perform an action planning process (56). In this way, the decision-making process may comprise steps of sizing an opportunity for the healthcare provider to increase the number of times the healthcare provider provides the medical therapy, analyzing effects of the one or more barriers to the patients receiving the medical therapy from the healthcare provider, prioritizing the one or more barriers, and formulating an action plan for reducing at least one of the one or more barriers.

During the opportunity sizing process (50), the healthcare provider may determine the size of the healthcare provider's opportunity to provide the medical therapy. The size of the healthcare provider's opportunity to provide the medical therapy may indicate a difference between a total number of patients who are eligible to receive the medical therapy and the number of such patients who receive the medical therapy from the healthcare provider. FIGS. 4-7, described elsewhere in this disclosure, provide example user interfaces associated with the opportunity sizing process.

Figure 8:
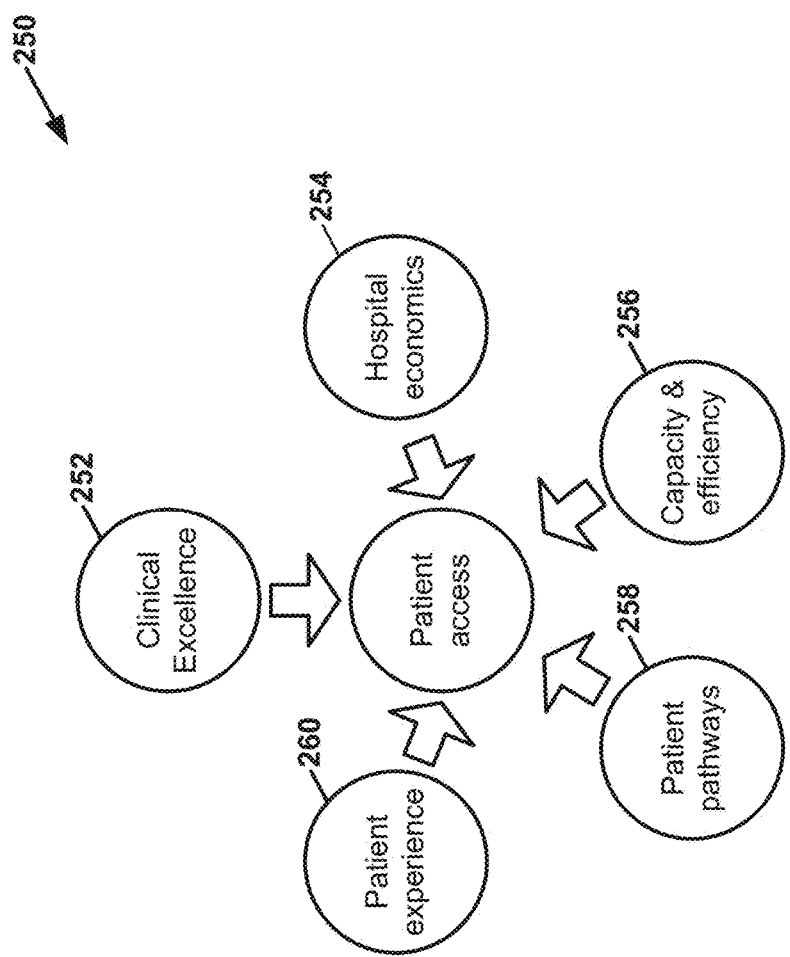
FIG. 8 is a conceptual diagram illustrating an example user interface associated with inputting barrier assessment data, in accordance with one or more techniques of this disclosure.
Figure 9:
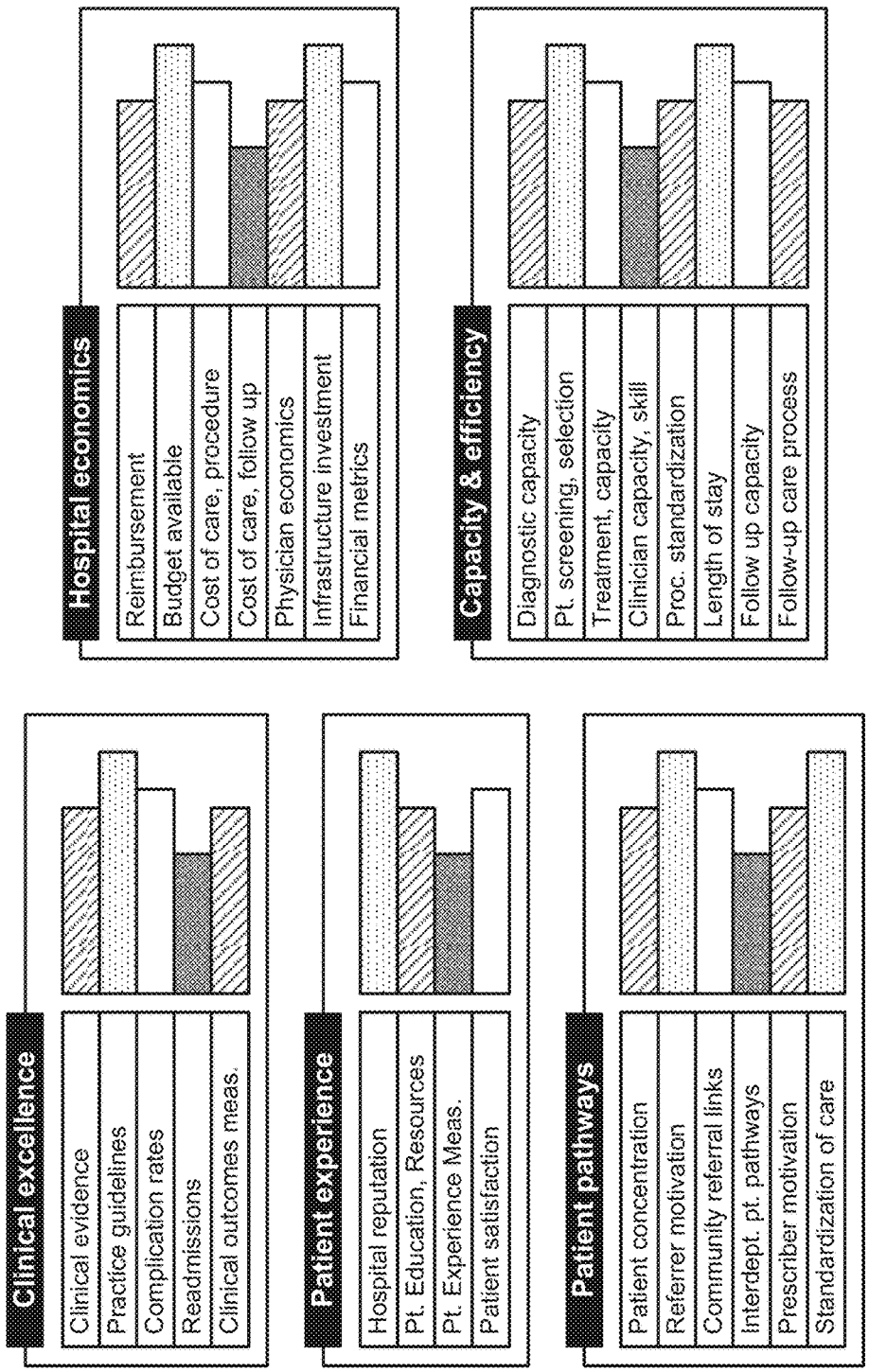
FIG. 9 is a conceptual diagram showing an example barrier assessment interface, in accordance with one or more techniques of this disclosure.

During the barrier assessment process (52), the healthcare provider may assess potential barriers to patients accessing the medical therapy from the healthcare provider. For instance, during the barrier assessment process, the healthcare provider may answer questions related to clinical excellence, hospital economics, capacity and efficiency, patient pathways, and patient experiences. Based on the answers to the questions, data processing unit 16 may generate data indicating relative impacts of various potential barriers to patients accessing the medical therapy from the healthcare provider. FIGS. 8 and 9, described elsewhere in this disclosure, provide example user interfaces associated with the barrier assessment process.

In any embodiment of the first through seventh aspects of the invention, during the barrier assessment process (52), computing system 10 may output, for display, a plurality of multiple-choice questions related to a plurality of barriers to patients receiving a medical therapy from a healthcare provider. The plurality of barriers may include barriers related to: clinical evidence, reimbursement, physician economics, physician capacity and training level for the medical therapy, treatment capacity, and so on. In any embodiment of the first through seventh aspects of the invention, barriers related to clinical evidence may prevent patients from accessing a medical therapy from a healthcare provider because there may be insufficient clinical evidence regarding patient outcomes of patients who have received the medical therapy from the healthcare provider. In any embodiment of the first through seventh aspects of the invention, barriers related to reimbursements may prevent patients from accessing a medical therapy from a healthcare provider because the healthcare provider may be unable to obtain sufficient reimbursement for providing the medical therapy. In any embodiment of the first through seventh aspects of the invention, barriers related to physician economics may prevent patients from accessing a medical therapy from a healthcare provider because may providing the medical therapy to the patients may not be economical for the physicians. In any embodiment of the first through seventh aspects of the invention, barriers related to physician capacity and training level for the medical therapy may prevent patients from accessing the medical therapy from the healthcare provider because physicians of the healthcare provider may have insufficient capacity or training to provide the medical therapy to the patients. In any embodiment of the first through seventh aspects of the invention, barriers related to treatment capacity may prevent patients from accessing the medical therapy from the healthcare provider because the healthcare provider's physical facilities may be insufficient to support current therapy volume and future growth.

Furthermore, in any embodiment of the first through seventh aspects of the invention, computing system 10 may receive indications of user input indicating selected answers to the multiple-choice questions. Each of the answers to the multiple-choice questions may correspond to a quantitative value. Computing system 10 may generate, based on the quantitative values corresponding to the selected answers, one or more diagrams indicating relative severity of the barriers in preventing the patients from receiving the medical therapy from the healthcare provider.

Figure 11:
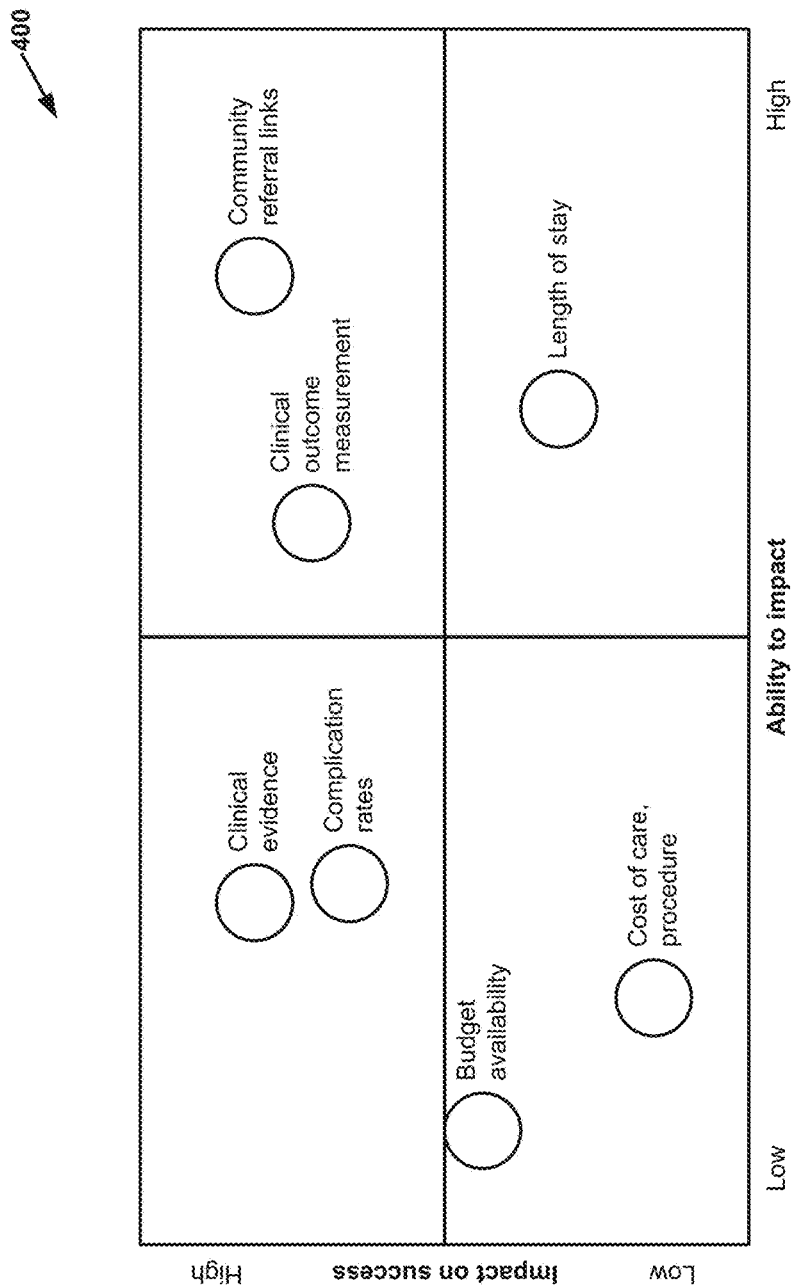
FIG. 11 is a conceptual diagram illustrating an example barrier prioritization matrix, in accordance with one or more techniques of this disclosure.

During the barrier prioritization process (54), the healthcare provider may use data generated by data processing unit 16 to prioritize barriers to patients accessing the medical therapy from the healthcare provider. For example, data processing unit 16 may generate data indicating the relative ability of the healthcare provider and the relative impact of success of the healthcare provider addressing particular barriers. FIGS. 10 and 11, described elsewhere in this disclosure, provide example user interfaces associated with the barrier prioritization process.

Figure 12:
FIG. 12 is a conceptual diagram illustrating an example action planning interface, in accordance with one or more techniques of this disclosure.

During the action planning process (56), the healthcare provider may formulate a plan for addressing one or more of the barriers. For example, the healthcare provider may determine strategies for addressing particular barriers, may identify executional milestones for the identified strategies, and may identify investment needs to execute the identified strategies. FIG. 12, described elsewhere in this disclosure, provides an example user interface associated with the action planning process.

Figure 3:
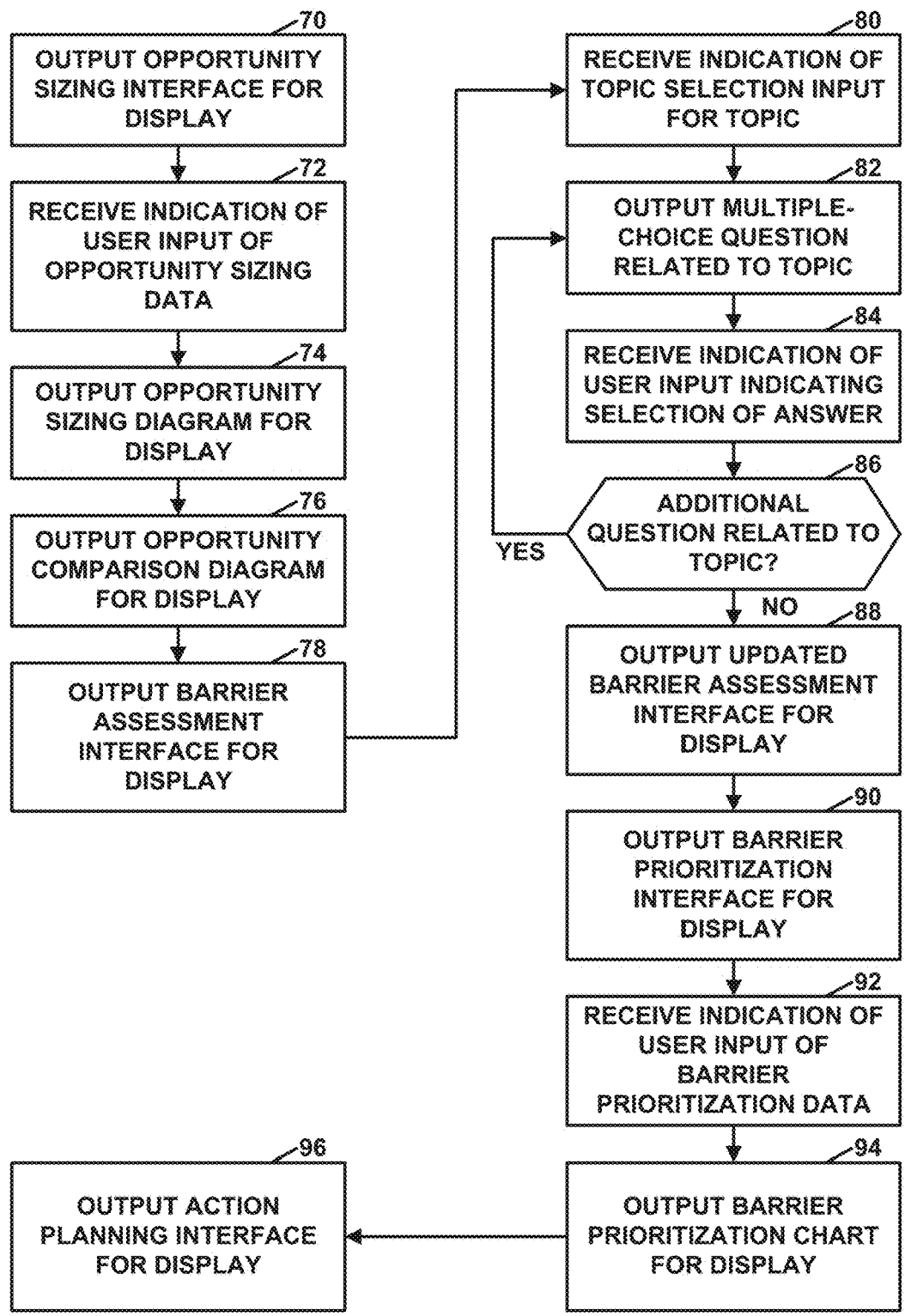
FIG. 3 is a flowchart illustrating an example operation performed by a computing system, in accordance with one or more techniques of this disclosure.
Figure 5:
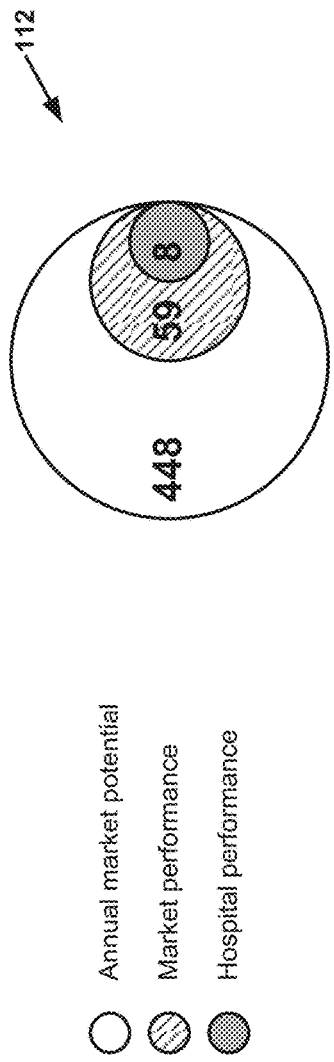
FIG. 5 is a conceptual diagram illustrating a second portion of the example opportunity sizing interface, in accordance with one or more techniques of this disclosure.

FIG. 3 is a flowchart illustrating an example operation of computing system 10, in accordance with one or more techniques of this disclosure. In the example of FIG. 3, data processing unit 16 of computing system 10 may output an opportunity sizing interface for display (70). In this disclosure, outputting data (e.g., an interface) for display may involve outputting data to a device (e.g., a display device that may or may not be connected physically to the outputting device) may display the data or further process the data for display by another device. FIGS. 4 and 5, described in detail elsewhere in this disclosure, are conceptual diagrams illustrating an example opportunity sizing interface. The opportunity sizing interface may include features that enable a user to input (and for data processing unit 16 to receive) opportunity sizing input data. The opportunity sizing input data may include quantitative data related to population size, prevalence of a medical condition treatable by the medical therapy, and so on. Furthermore, data processing unit 16 may receive one or more indications of user input of opportunity sizing input data (72). Data processing unit 16 may receive indications of user input from input device 12 and/or data storage system 14.

In any embodiment of the first through seventh aspects of the invention, the opportunity sizing data may be obtained automatically. Data related to population size may be obtained directly by the system from the internet. Likewise, data indicating the prevalence of a medical condition treatable by therapy can be obtained directly from the internet.

Figure 6:
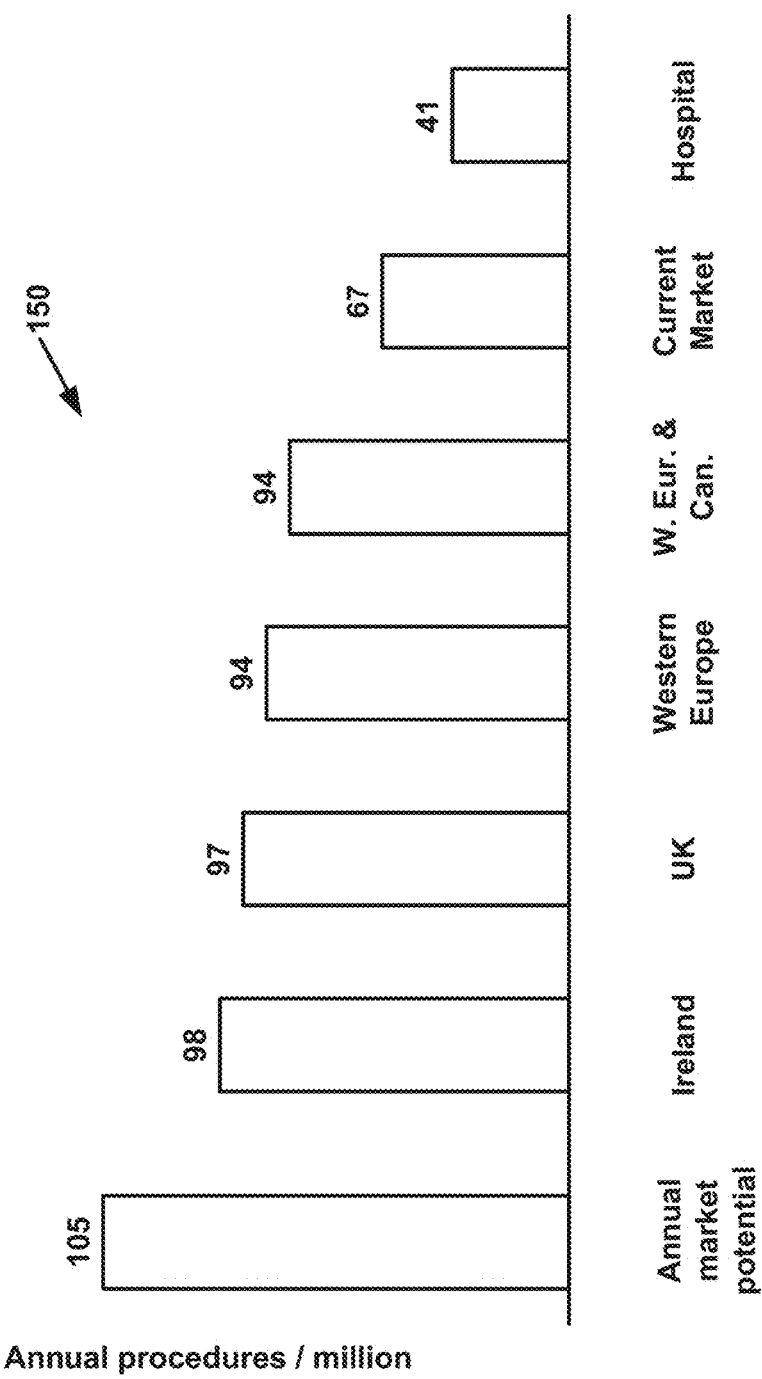
FIG. 6 is a conceptual diagram illustrating an example opportunity sizing diagram, in accordance with one or more techniques of this disclosure.
Figure 7:
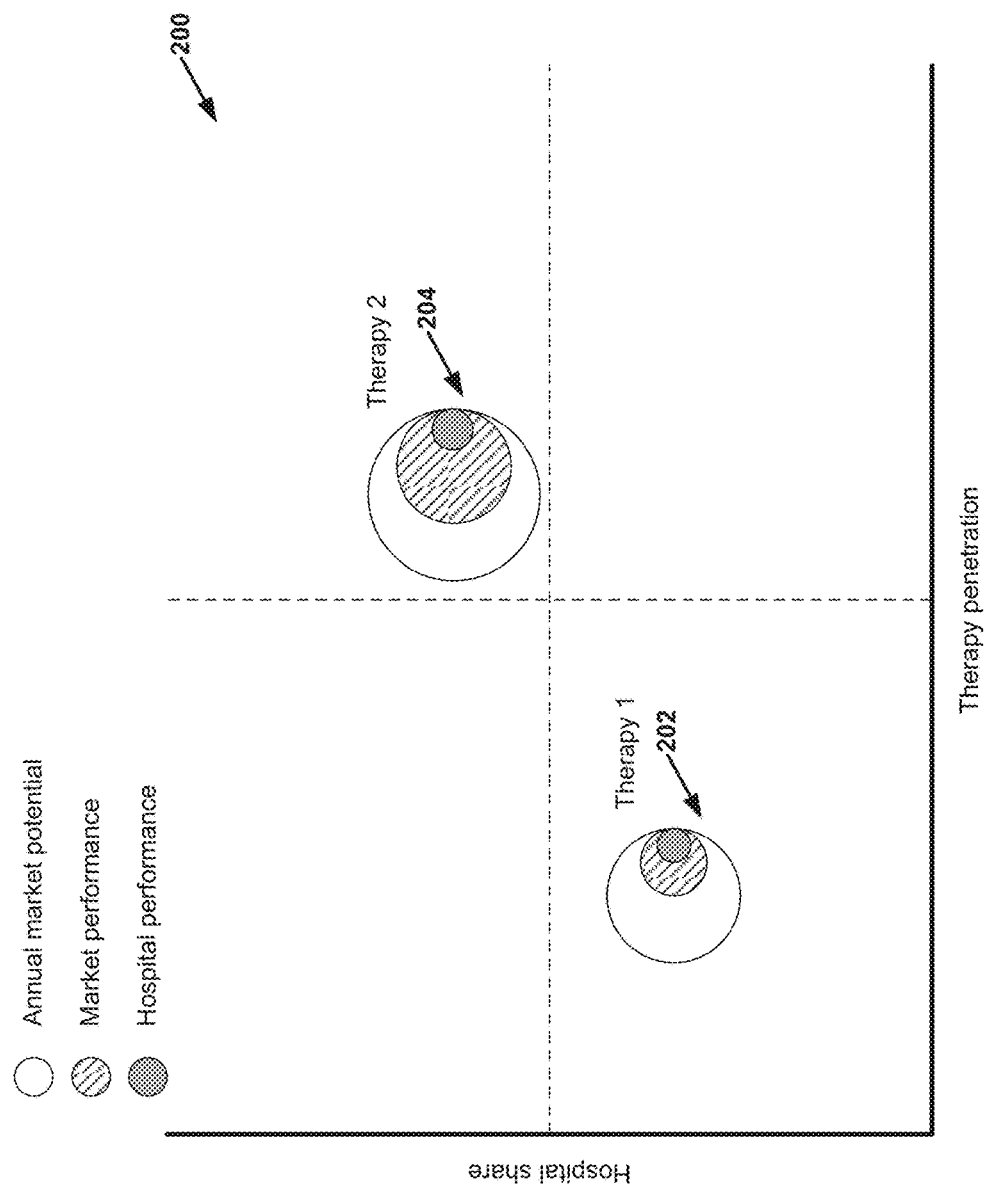
FIG. 7 is a conceptual diagram illustrating an example opportunity comparison diagram, in accordance with one or more techniques of this disclosure.

In addition, data processing unit 16 may output one or more opportunity sizing diagrams for display (74). FIG. 6, described in detail elsewhere in this disclosure, is a conceptual diagram illustrating an example opportunity sizing diagram. The opportunity sizing diagram may enable a user to compare the number of times the hospital provides the medical therapy with the number of times the hospital theoretically could be providing the medical therapy. Furthermore, data processing unit 16 may output an opportunity comparison diagram for display (76). FIG. 7, described in detail elsewhere in this disclosure, is a conceptual diagram illustrating an example opportunity comparison diagram. The opportunity comparison diagram may include features for comparing medical therapies for barrier reduction.

Subsequently, data processing unit 16 may output a barrier assessment interface for display (78). In any embodiment of the first through seventh aspects of the invention, barriers to patients accessing the medical therapy from the hospital may be categorized into a plurality of topics. In any embodiment of the first through seventh aspects of the invention, the topics may include clinical excellence, hospital economics, capacity and efficiency, patient pathways, patient experience, and other categories of barriers. The barrier assessment interface may include user-selectable features corresponding to respective topics in the plurality of topics. FIG. 8, described in detail elsewhere in this disclosure, illustrates example user-selectable features corresponding to respective topics. Furthermore, while the barrier assessment interface is displayed, data processing unit 16 may receive an indication of topic selection input for a topic (80). For instance, data processing unit 16 may receive an indication of a user selection of a user-selectable feature corresponding to the topic.

Responsive to the topic selection input, data processing unit 16 may output a multiple-choice barrier assessment question related to the topic (82). Furthermore, data processing unit 16 may receive an indication of user input indicating a selection of one of the answers to the multiple-choice barrier assessment question (84). For example, each of the potential answers to the multiple-choice barrier assessment question may correspond to a respective radio button. In this example, data processing unit 16 may receive an indication of user input indicating a selection of one of the answers when data processing unit 16 receives an indication of a user selection of the radio button corresponding to the answer. Subsequent to receiving an indication of user input indicating a selection of one of the answers, data processing unit 16 may determine whether there are any additional barrier assessment questions related to the topic (86). If there are one or more additional barrier assessment questions related to the topic ("YES" of 86), data processing unit 16 may repeat actions 82-86 with another barrier assessment question related to the topic.

However, if there are no additional barrier assessment questions related to the topic ("NO" of 86), data processing unit 16 may output an updated version of the barrier assessment interface for display (88). The updated version of the barrier assessment interface may include one or more diagrams indicating results of barrier assessment questions related to the topics. FIG. 9, described in detail elsewhere in this disclosure, illustrates example diagrams indicating results of barrier assessment questions related to particular topics of barriers to patients accessing a medical therapy from the hospital. While the updated version of the barrier assessment interface is displayed, data processing unit 16 may repeat actions 80-88 with regard to another one of the topics.

Subsequently, data processing unit 16 may output a barrier prioritization interface for display (90). The barrier prioritization interface may include data entry features for receiving input of data for prioritizing barriers (i.e., barrier prioritization data). In any embodiment of the first through seventh aspects of the invention, the barrier prioritization data for a barrier may include a quantitative value correlated with the ability of the hospital to reduce the barrier and a quantitative value correlated with the estimated impact that reducing the barrier would have on increasing patient access to receiving the medical therapy from the hospital. FIG. 10, described in detail elsewhere in this disclosure, illustrates an example barrier prioritization interface. While the barrier prioritization interface is displayed, data processing unit 16 may receive an indication of user input of the barrier prioritization data (92).

Furthermore, in the example of FIG. 3, data processing unit 16 may output a barrier prioritization chart for display (94). FIG. 11, described in detail elsewhere in this disclosure, illustrates an example barrier prioritization chart. The barrier prioritization chart may include features that enable the hospital to compare relative priorities of barriers. Data processing unit 16 may generate the barrier prioritization chart based at least in part on the previously-received barrier prioritization data.

Subsequently, data processing unit 16 may output an action planning interface for display (96). The action planning interface may correspond to the action planning process (56) of FIG. 2. FIG. 12, described in detail elsewhere in this disclosure, is an example of an action planning interface. The action planning interface may include data input features for input of data related to strategies for reducing one or more of the barriers to patients accessing the medical therapy from the hospital.

FIG. 4 is a conceptual diagram illustrating a first portion of an example opportunity sizing interface, in accordance with one or more techniques of this disclosure. As indicated above, data processing unit 16 may receive various types of data to determine the size of a hospital's opportunity to provide a medical therapy. In the example of FIG. 4, the opportunity sizing interface accepts user input of quantitative data (i.e., opportunity sizing input data) in shaded cells.

For instance, in the example of FIG. 4, data processing unit 16 may receive data indicating a total population size of a country and data indicating a gross indicated prevalence of a medical condition treatable by the medical therapy. Based on the total population size of the country and the data indicating the gross indicated prevalence, data processing unit 16 may calculate the prevalence per million and may output the calculated prevalence per million for display in the "per million" cell in the gross indicated prevalence row. For instance, in the example of FIG. 4, the user has inputted "4,585,000" as the country population and inputted "9,558" as the gross indicated prevalence. Accordingly, data processing unit 16 may output "2,085" for display in the "per million" cell in the gross indicated prevalence row. As described herein, in any embodiment, the data processing unit can be configured to electronically receive data regarding the population of a geographic area and the prevalence of a medical condition treatable by the medical therapy.

Furthermore, data processing unit 16 may receive data indicating a total population of a service area for the hospital. The service area for the hospital may be a geographic region served by the hospital. In the example of FIG. 4, the user has inputted "850,000" as the total population of the service area for the hospital. In addition, data processing unit 16 may receive data indicating a clinical exclusion percentage and an economic exclusion percentage. The clinical exclusion percentage indicates a percentage of patients having a medical condition treatable by the medical therapy but who also have a condition that makes the medical therapy inadvisable for the medical condition. Examples of clinical exclusion may include advanced age, co-morbidity, such as late stage cancer, where the patient is unlikely to benefit from the medical therapy, tortuous venous structure that prevents the medical therapy from being performed, and so on. The economic exclusion percentage indicates a percentage of the indicated patient population (i.e., members of the population having the medical condition treatable by the medical therapy) who do not have access to the medical therapy because of economic factors. Such economic factors may include lack of public or private health insurance, lack of disposable income to pay patient's share of cost (e.g., co-payment), the medical therapy not being available locally and impracticality of traveling to a location where the medical therapy is available due to distance and/or lack of transportation infrastructure, patients served by healthcare systems not compliant with standards, and so on. In the example of FIG. 4, the user has inputted "20%" and "5%" as the clinical exclusion percentage and the economic exclusion percentage, respectively.

Data indicative of clinical exclusion can, in any embodiment, be generated automatically by the data processing unit 16. The incidence of advanced age, co-morbidities, and other clinical exclusion data can be estimated from publically or privately available data concerning patients with the medical condition treatable by the medical therapy. This information can be directly received from the internet or other source by the data processing unit 16. Similarly, in any embodiment, data indicative of economic exclusion can automatically be received by data processing unit 16. The percentage of the population in the geographic area with insurance can be obtained electronically from public or private sources and automatically be received by data processing unit 16. Income information can also be obtained electronically by the data processing unit 16. In any embodiment, the data processing unit 16 can obtain information indicative of clinical or economic exclusion periodically from external sources and automatically updated each month, year or set number of years.

Based on the population of the service area, the gross indicated prevalence per million, the clinical exclusion percentage and the economic exclusion percentage, data processing unit 16 may calculate a net indicated prevalence and a net indicated prevalence per million. The net indicated prevalence may indicate the number of individuals in the hospital's service area who have the medical condition and are not subject to clinical exclusions or economic exclusions. The net indicated prevalence per million may indicate the prevalence of individuals in the hospital's service area who have the medical condition and are not subject to clinical exclusions or economic exclusions, per million. For instance, in the example of FIG. 4, data processing unit 16 calculates the net indicated percentage and the net indicated prevalence per million as 1,375 and 1,618 respectively.

Furthermore, data processing unit 16 may receive data indicating an expected life span of an individual who has the condition treatable by the medical therapy. The expected life span with the condition may indicate the average time an individual spends with this particular indication (i.e., the condition treatable by the medical therapy). In the example of FIG. 4, the user has inputted "4.5" as the expected life span of an individual who has the condition treatable by the medical therapy. In any embodiment, data processing unit 16 may automatically receive data indicating an expected life span of an individual with the condition treatable by the medical therapy automatically. Data concerning the expected life span of individuals with treatable conditions may be available over the internet from public or private sources. The data processing unit 16 can be configured to obtain and periodically update this information automatically.

Data processing unit 16 may determine a net indicated incidence and may output the net indicated incidence for display in the input column of the net indicated incidence row. The net indicated incidence may be the number of people who develop an indication (i.e., a medical condition treatable by the medical therapy) in a typical 12-month period. Data processing unit 16 may calculate a gross indicated incidence from the net indicated prevalence and the life span with the condition. For instance, the net indicated incidence may be the gross incidence minus clinical exclusion and economic exclusion. In any embodiment of the first through seventh aspects of the invention, data processing unit 16 may determine the net indicated incidence (i.e., an estimate of the number of applicable individuals) in accordance with the techniques described in U.S. Provisional Patent Application 61/876,591, the entire content of which is incorporated herein by reference. In the example of FIG. 4, data processing unit 16 may determine that the net indicated incidence and the net indicated incidence per million are 306 and 356, respectively.

In addition, data processing unit 16 may receive data indicating an average number of years an individual spends with the medical therapy. In any embodiment of the first through seventh aspects of the invention where the medical therapy comprises a medical device, data processing unit 16 may also receive data indicating a longevity for the device (i.e., a device longevity). The device longevity may indicate how long the medical device typically lasts before needing to be replaced. In the example of FIG. 4, the user has inputted 7.1 as the average number of years an individual spends with the medical therapy. Data indicating an average number of years an individual spends with medical therapy may be obtained without human involvement. For example, clinical research may already be available with this data. Data processing unit 16 may be configured to obtain this data from public or private sources automatically, and to periodically update this data.

Furthermore, data processing unit 16 may calculate a new procedures potential. The new procedures potential may indicate the potential number of procedures (e.g., administrations of the medical therapy) when the medical therapy reaches a standard of care. For example, the new procedures potential may indicate whichever is greater of the net indicated incidence or 15% of the difference between the net indicated prevalence and the treated prevalence in region. Data processing unit 16 may output the new procedures potential for display in the new procedures potential row of the opportunity sizing interface. In the example of FIG. 4, data processing unit 16 has calculated the new procedures potential and the new procedures potential per million as 306 and 359, respectively.

In the example of FIG. 4, the medical therapy comprises a medical device. Accordingly, in the example of FIG. 4, data processing unit 16 may calculate a replacement percentage and may output the replacement percentage for display. The replacement percentage may indicate the percentage of installed medical devices that are likely to be replaced in a typical year. Data processing unit 16 may determine the replacement percentage based on the average years on therapy and device longevity. The example of FIG. 4, assumes that treated patients who live longer than their medical device are those patients who receive replacements. In addition, data processing unit 16 may determine a replacements potential and may output the replacement potential for display. The replacement potential may indicate the number of replacements of the medical device performed in a typical year. The replacement potential may be equal to 0.5 multiplied by the net indicated prevalence multiplied by the replacement percentage. In the example of FIG. 4, the user has inputted the value 4.0 as the device longevity. Data processing unit 16 may obtain device longevity data automatically as opposed to through user input. Manufacturers of devices for treating a medical condition may make available data concerning device longevity. Data processing unit 16 may obtain this data from the internet, or from the manufacturers directly. Because more than one device may be usable for a single medical condition, data processing unit 16 may obtain data of device longevity for multiple medical devices that can be used to treat a particular condition.

Accordingly, in the example of FIG. 4, data processing unit 16 has calculated the replacement percentage as 10.9%, the replacements potential as 75, and the replacements potential per million as 88.

Furthermore, in the example of FIG. 4, data processing unit 16 may determine a total annual potential and may output the total annual potential for display. The total annual potential may be equal to the initial procedures plus replacement procedures. For instance, the total annual potential may be equal to the replacements potential plus the new procedures potential. In the example of FIG. 4, data processing unit 16 has determine that 381 is the total annual potential and that 448 is the total annual potential per million.

In the example of FIG. 4, data processing unit 16 may receive and store notes for each of the country population, gross indicated prevalence, population of service area, clinical exclusion, net indicated prevalence, life span with condition, net indicated incidence, average years on therapy, new procedures potential, device longevity, replacement percentage, replacements potential, and total annual potential.

Furthermore, in the example of FIG. 4, data processing unit 16 may receive and store benchmarking data (i.e., Benchmarking comparison points) in data entry cells 100. The benchmarking data may include data indicating countries or regions and, for each respective country or region, a respective number of procedures (e.g., medical therapies) performed per million residents of the respective country or region. In this and other examples, discussion of "procedures" may be applicable in some examples to medical therapies. In the example of FIG. 4, the user has inputted "Ireland," "UK," "Western Europe," and "W. Eur. & Can." as benchmark countries/regions. Furthermore, the user has inputted, as number of procedures per million inhabitants, "85," "84," "82," and "80" for "Ireland," "UK," "Western Europe," "W. Eur. & Can.," respectively. In any embodiment, data processing unit 16 may receive benchmarking data automatically. The number of procedures performed in various countries or regions may be available from the internet. Data processing unit 16 may receive this data from the internet periodically.

FIG. 5 is a conceptual diagram illustrating a second portion of the example opportunity sizing interface, in accordance with one or more techniques of this disclosure. In the example of FIG. 5, the opportunity sizing user interface includes a set of cells 110 for entry and display of data related to current market performance within the service area of the hospital. Specifically, in the example of FIG. 5, data processing unit 16 may receive historical data indicating the annual number of procedures performed in an entire market served by the hospital (i.e., the service area of the hospital) in particular years. Furthermore, data processing unit 16 may determine, based on the annual market procedures, the procedures performed yearly in the service area of the hospital. In addition, data processing unit 16 may determine, and output for display in cells 110, the number of yearly procedures performed in the service area of the hospital per million inhabitants of the service area of the hospital. Data processing unit 16 may determine this value by dividing the number of yearly procedures performed in the service area of the hospital by one million multiplied by the population of the service area. In the example of FIG. 5, data processing unit 16 may determine the number of procedures performed yearly in the service area of the hospital to be 50 and may determine the number of yearly procedures performed in the service area of the hospital per million inhabitants of the service area of the hospital to be 59.

Furthermore, data processing unit 16 may receive and output for display data indicating the number of times the hospital performs the procedure yearly. In the example of FIG. 5, data processing unit 16 may determine, and output for display in cells 110, the number of times the hospital performs the procedure yearly, per million individuals in the service area of the hospital. Data processing unit 16 may determine the number of times the hospital performs the procedure yearly by dividing the number of times the hospital performs the procedure yearly by one million multiplied by the population of the service area of the hospital. In the example of FIG. 5, the user has inputted 7 as the number of times the hospital performs the procedure yearly. In any embodiment of the first through seventh aspects of the invention, the number of times the hospital performs the procedure may be obtained automatically from hospital records. Accordingly, in the example of FIG. 5, data processing unit 16 may determine that the number of times the hospital performs the procedure yearly per million individuals in the service area of the hospital to be 8.

In any embodiment of the first through seventh aspects of the invention, the number of times the healthcare provider provides the therapy may be obtained electronically without the use of medical records. Devices used in medical therapy can be configured to automatically send a signal, wirelessly or through wired communication, to the system each time the device is used. For example, if the medical therapy is dialysis, the dialysis machine can be configured to send a signal the system each time dialysis is performed in a patient. The system can then automatically update the number of times the healthcare provider has provided the medical therapy. Alternatively, each time a medical therapy is performed by the hospital, a user can send an electronic signal to the system updated the system data concerning the number of times the medical therapy has been performed. The signals can be sent wirelessly to a receiver connected to the system, through manual input, such as with a keyboard, or over the internet.

In addition, data processing unit 16 may receive and output for display data indicating the percentage of the procedures performed by the hospital that are replacement procedures. Data processing unit 16 may obtain this data automatically from the hospital records. Data processing unit 16 may also determine, and output for display in cells 110, a hospital procedure share percentage. Data processing unit 16 may determine the hospital procedure share percentage by dividing the number of times the hospital performs the procedure yearly by the number of times the procedure is performed yearly in the service area of the hospital. In the example of FIG. 5, the user has inputted 10.0% as the percentage of procedures performed by the hospital that are replacement procedures. Accordingly, data processing unit 16 may determine that the hospital procedure share percentage is 14%.

In the example of FIG. 5, data processing unit 16 may also determine, and output for display in cells 110, a treated prevalence in the region (i.e., service area of the hospital) and a treated prevalence in the region per million inhabitants of the region. Furthermore, data processing unit 16 may determine, and output for display in cells 110, a penetration of net prevalence. Data processing unit 16 may determine the penetration of net prevalence by dividing the treated prevalence in the region served by the hospital by the net indicated prevalence. The penetration of net prevalence is the number of people in an indicated pool receiving treatment divided by the total number in the indicated pool treated and untreated. In the example of FIG. 5, data processing unit 16 may determine that the treated prevalence in the region is 130, the treated prevalence in the region per million inhabitants of the region is 153, and that the penetration of net prevalence is 9%.

The data entered into cells of the opportunity sizing interface of FIGS. 4 and 5 may be examples of opportunity sizing input data. However, the term opportunity sizing input data may also apply to other input data used for opportunity sizing and may be different in one or more ways from the data entered into the cells of the opportunity sizing interface of FIGS. 4 and 5.

Based on data entered in the user interface for receiving opportunity sizing data (i.e., the opportunity sizing input data), data processing unit 16 may generate and output for display one or more diagrams for visualization of the opportunity sizing data. In other words, data processing unit 16 may generate and output for display one or more opportunity sizing diagrams. In the example of FIG. 5, data processing unit 16 may generate, and output for display in the interface, a bubble chart 112 showing relative sizes of the annual market potential per million inhabitants of the service area of the hospital, market performance per million inhabitants of the service area of the hospital, and hospital performance per million inhabitants of the service area of the hospital. The hospital performance per million inhabitants of the service area of the hospital may be equal to the number of times the hospital performs the procedure yearly, per million inhabitants of the service area of the hospital. In any embodiment of the first through seventh aspects of the invention, the same information may be presented in a bar graph form. Furthermore, any embodiment of the first through seventh aspects of the invention, the opportunity sizing interface may include a control for switching between the bubble chart view and the corresponding bar graph. In any embodiment of the first through seventh aspects of the invention, the data processing unit 16 may generate and output displays other than the bubble charts described. One skilled in the art will understand that the output may be alternatively displayed as a text-based listing of the same data.

In any embodiment of the first through seventh aspects of the invention, a consultant may assist the hospital with the decision-making process. In any embodiment of the first through seventh aspects of the invention, the consultant may be responsible for determining and/or inputting data for the country population, gross indicated prevalence, clinical exclusion, economic exclusion, life span with condition, average years on therapy, device longevity, and annual market procedures. In any embodiment of the first through seventh aspects of the invention, the hospital may determine and/or input the remaining opportunity sizing data, such as the population of the service area, the yearly procedures performed by the hospital, and the percentage of replacement procedures.

FIG. 6 is a conceptual diagram illustrating an example opportunity sizing diagram 150, in accordance with one or more techniques of this disclosure. Data processing unit 16 may generate opportunity sizing diagram 150 and may output opportunity sizing diagram 150 for display as part of the opportunity sizing process (50) of FIG. 2. Data processing unit 16 may generate opportunity sizing diagram 150 based on opportunity sizing input data received in the opportunity sizing interface of FIGS. 4 and 5. In any embodiment of the first through seventh aspects of the invention, data processing unit 16 may generate opportunity sizing diagram 150 based on data generated from the opportunity sizing input data received in the opportunity sizing interface of FIGS. 4 and 5. In any embodiment of the first through seventh aspects of the invention, the data processing unit 16 may generate and output displays other than the diagrams described. One skilled in the art will understand that the output may be alternatively displayed as a text-based listing of the same data.

In the example of FIG. 6, opportunity sizing diagram 150 may indicate the annual market potential for the medical therapy, the number of times the medical therapy is performed yearly per million inhabitants of one or more benchmark countries or regions, the number of times the medical therapy is performed yearly per million inhabitants of a current market served by the hospital, and the number of times the medical therapy is performed by the hospital yearly per million inhabitants of the market served by the hospital. Although in the example of FIG. 6 opportunity sizing diagram 150 includes data for multiple benchmark countries or regions, opportunity sizing diagram 150 may, in any embodiment of the first through seventh aspects of the invention, include data for no benchmark countries or regions or for a single benchmark country or region.

In the example of FIG. 6, opportunity sizing diagram 150 indicates the annual procedures performed per million inhabitants for Ireland, the UK, Western Europe, Western Europe & Canada, for the current market area of the hospital, and for the hospital. FIG. 6 includes data for the benchmark regions of Ireland, the UK, Western Europe, and Western Europe and Canada because benchmark data for these benchmark regions was entered in data entry cells 100 of the opportunity sizing interface of FIG. 4. In addition, the opportunity sizing diagram 150 of FIG. 6 indicates an annual market potential for the medical therapy in terms of annual procedures per million inhabitants of the service area of the hospital.

In any embodiment of the first through seventh aspects of the invention, if computing system 10 has received opportunity sizing data in the opportunity sizing interface (e.g., the opportunity sizing interface of FIGS. 4 and 5) for additional medical therapies, opportunity sizing diagram 150 of FIG. 6 may concurrently include similar bar charts for the other medical therapies. This may help the hospital assess the relative sizes of the opportunities to reduce barriers to the medical therapies.

As indicated above, the decision-making process may comprise determining whether to reduce the one or more barriers to the patients receiving the medical therapy from the healthcare provider. Thus, in the manner described with regard to FIG. 6 and in the manner described with regard to bubble chart 110 of FIG. 5, data processing unit 16 may receive quantitative data and may generate, based on at least some of the received quantitative data, a diagram that enables a comparison of a number of times the healthcare provider provides the medical therapy in a time period with a potential number of times the medical therapy could be provided in the time period to individuals inhabiting a service area for the healthcare provider.

More specifically, in the example of FIG. 6, data processing system 16 may determine, based on received quantitative data, the potential number of times the medical therapy could be provided in the time period to individuals inhabiting the service area for the healthcare provider, determine, based on the quantitative data, a number of times the medical therapy is typically administered in the time period in a region other than the service area, and determine, based on the quantitative data, a number of times the medical therapy is typically administered in the service area in the time period.

Furthermore, in the example of FIG. 6, the diagram is a graph (e.g., a bar graph) indicating (e.g., via a first bar) the potential for providing the medical therapy in the time period for individuals inhabiting the service area, indicating (e.g., via a second bar) the number of times the medical therapy is typically administered in the time period in the region other than the service area, indicating (e.g., via a third bar) the number of times the medical therapy is typically administered in the service area in the time period, and indicating (e.g., via a fourth bar) the number of times the healthcare provider provides the medical therapy in the time period.

FIG. 7 is a conceptual diagram illustrating an example opportunity comparison diagram 200, in accordance with one or more techniques of this disclosure. As previously indicated, a hospital may provide several different types of medical therapies and there may be barriers to patients accessing each of these medical therapies from the hospital. Because the hospital may only have limited resources, the hospital may need to choose one of the medical therapies on which to focus its barrier-reduction efforts. In the example of FIG. 7, opportunity comparison diagram 200 comprises a bubble chart that may help the hospital choose one of the medical therapies on which to focus its barrier-reduction efforts. In any embodiment of the first through seventh aspects of the invention, the data processing unit 16 may generate and output displays other than the bubble chart described. One skilled in the art will understand that the output may be alternatively displayed as a text-based listing of the same data.

Opportunity comparison diagram 200 includes sets of bubbles corresponding to particular medical therapies. The sets of bubbles are positioned vertically within opportunity comparison diagram 200 according to the hospital's share of the annual market for medical therapies corresponding to the sets of bubbles. The sets of bubbles are positioned horizontally within opportunity comparison diagram 200 according to the therapy penetration of the medical therapies corresponding to the sets of bubbles. The therapy penetration may indicate the number of people who receive the medical therapy. For each respective medical therapy, the set of bubbles corresponding to the respective medical therapy may indicate relative sizes of the annual market potential for a respective medical therapy per million inhabitants of the service area of the hospital, market performance for the respective medical therapy per million inhabitants of the service area of the hospital, and hospital performance for the respective medical therapy per million inhabitants of the service area of the hospital. In the example of FIG. 7, opportunity comparison diagram 200 includes a set of bubbles 202 for Therapy 1 and a set of bubbles 204 for Therapy 2.

By reviewing opportunity comparison diagram 200, the hospital can determine the medical therapies on which to focus its barrier-reduction efforts. For instance, the hospital may determine, based on opportunity comparison diagram 200, to focus its barrier-reduction efforts on medical therapies where the hospital has a low market share, the therapy penetration is low, and the annual market potential is significantly greater than the current market performance.

In any embodiment of the first through seventh aspects of the invention, the system may utilize algorithms to suggest particular therapies on which the hospital should concentrate barrier reduction efforts. For example, the system may compare hospital market share, therapy penetration and market potential across multiple therapies. The quantitative values for each of the data may used by the system to determine therapies where barrier reduction efforts may make the most difference. For example, the system may multiply the market potential by the inverse of hospital market share in order to obtain a score that is greater in situations with a significant market potential by a low hospital market share. This allows for a sliding scale of scores taking into account the multiple quantitative data sources in order to determine where the hospital should focus barrier reduction efforts.

As indicated elsewhere in this disclosure, the decision-making process may comprise determining whether to reduce the one or more barriers to the patients receiving the first medical therapy from a healthcare provider or whether to reduce one or more barriers to the patients receiving a second medical therapy from the healthcare provider. Furthermore, data processing unit 16 may, as part of generating data targeted to facilitating the decision-making process, generate, based on received quantitative data, a diagram (e.g., opportunity comparison diagram 200) that enables a comparison of a size of an opportunity for the healthcare provider to increase the number of times the healthcare provider provides the first medical therapy with a size of an opportunity for the healthcare provider to increase the number of times that the healthcare provider provides the second medical therapy. In any embodiment of the first through seventh aspects of the invention, the system can allow comparison of more than two therapies. In any embodiment of the first through seventh aspects of the invention, the data processing unit 16 may create a diagram enabling a comparison of a size of an opportunity for the healthcare provider to increase the number of times the healthcare provides a therapy between 3, 4, 5, 6, 7, 8, 9, 10 or more therapies.

Furthermore, any embodiment of the first through seventh aspects of the invention, data processing unit 16 may determine, based on the quantitative data, a market share of the healthcare provider in providing the first medical therapy in a service area of the healthcare provider (e.g., the annual market potential). In addition, data processing unit 16 may determine, based on the quantitative data, a market share of the healthcare provider in providing the second medical therapy in the service area of the healthcare provider. In any embodiment of the first through seventh aspects of the invention, data processing unit 16 may determine a market share of the healthcare provider in providing a third, fourth, fifth, sixth, seventh, eighth, ninth, tenth and more therapies. Furthermore, data processing unit 16 may determine, based on the quantitative data, a therapy penetration for the first medical therapy and a therapy penetration for each additional medical therapy. The diagram comprises a first set of bubbles for the first medical therapy and a second set of bubbles for the second medical therapy. The first set of bubbles is positioned within the diagram based on the market share of the healthcare provider in providing the first medical therapy in the service area and the therapy penetration for the first medical therapy. The second and subsequent sets of bubbles are positioned within the diagram based on the market share of the healthcare provider in providing the second and subsequent medical therapies in the service area and the therapy penetration for the second and subsequent medical therapy.

FIG. 8 is a conceptual diagram illustrating an example user interface 250 associated with inputting barrier assessment data, in accordance with one or more techniques of this disclosure. User interface 250 may be a portion of a barrier assessment interface. As shown in the example of FIG. 8, user interface 250 includes user-selectable elements 252, 254, 256, 258, and 260. Each of user-selectable elements 252, 254, 256, 258, and 260 corresponds to a different topic related to barriers to patients receiving a medical procedure from a particular hospital. In the example of FIG. 8, user-selectable element 252 corresponds to clinical excellence, user-selectable element 254 corresponds to hospital economics, user-selectable element 256 corresponds to capacity and efficiency, user-selectable element 258 corresponds to patient pathways, and user-selectable element 260 corresponds to patient experience.

The potential barriers to patients receiving a medical therapy from the hospital may be categorized by topic. In any embodiment of the first through seventh aspects of the invention, potential barriers associated with the topic of clinical excellence include clinical evidence, practice guidelines, complication rates, readmissions, and clinical outcome measurements. One skilled in the art will understand that each of the potential barriers listed can be further broken down into additional barriers. For example, complication rates can be broken down into complication rates at implantation of a medical device, and complication rates post implantation. Clinical outcome measurements can include the quality of life for the patient, procedure introduction success rates, procedure efficacy, the relative invasiveness of the procedure, and product reliability or performance both pre-implantation and post-implantation in the case of medical devices. Any factors associated with the above barriers are contemplated by the first through seventh aspects of the invention.

Potential barriers associated with the topic of hospital economics include reimbursement, budget availability, cost of care for the procedure, cost of care for follow up for the procedure, physician economics, infrastructure investment, and financial metrics. Potential barriers associated with the topic of capacity and efficiency include diagnostic capacity, patient screening and selection, treatment capacity, clinician capacity and skill, procedure standardization, length of stay, follow up capacity, and the follow up care process. Other potential barriers related to hospital economics can include the cost effectiveness of the therapy, return on therapy investment, regulatory concerns with the therapy, Potential barriers associated with the topic of patient pathways may include patient concentration, patient awareness, referrer motivation, community referral links, interdepartmental patient pathways, prescriber motivation, and standardization of care.

Potential barriers associated with the topic of patient experience include hospital reputation, patient education and resources, patient experience measurements, patient motivation, patient perception of the therapy, patient advocacy, ongoing patient resources and support, total ongoing cost of care, and patient satisfaction.

Further potential barriers to a medical therapy can include marketing and sales synergy for the provider, targeting versus competing providers or therapies, and advantages in product lines and portfolios.

In response to receiving an indication of a user selection of one of user-selectable elements 252, 254, 256, 258, and 260, data processing unit 16 may output for display one or more barrier assessment questions related to the topic that corresponds to the selected user-selectable element. In any embodiment of the first through seventh aspects of the invention, each of the barrier assessment questions related to a topic may be a multiple-choice question. Each of the potential answers (i.e., responses) to the barrier assessment questions may correspond to a discrete, ordinal value. Thus, although the barrier assessment questions may be asking for subjective or qualitative data, the selected answers may actually correspond to quantitative data. Furthermore, in any embodiment of the first through seventh aspects of the invention, data processing unit 16 may present each of the barrier assessment questions related to a topic in a graphical user interface that includes text fields into which a user may enter (and data processing unit 16 may receive) notes describing a barrier (i.e., a barrier description) and/or other comments.

Based on the answers to the questions described herein, a barrier score may be generated. A barrier score can be a discrete value representing the sums of the values assigned to each of the answered questions. In any embodiment of the first through seventh aspects of the invention, the barrier score can relate to the sums of the values assigned to individual or specific groups of questions. The barrier score can be used as described herein to determine the best course of action for a healthcare provider to take in order to increase the number of times the healthcare provider provides a medical therapy.

As indicated above, user-selectable element 252 corresponds to the topic of clinic excellence. Cells in the left column of the following table include example potential barriers related to the topic of clinical excellence and cells in the right column of the following table include example multiple-choice barrier assessment questions related to the corresponding potential barrier.

| | |
|---|---|
| Clinical evidence | Is clinical evidence strong - reproducible and actionable - so that it can inform evidence-based practices? |
| | Clinical evidence is weak, with only safety and efficacy data available; outcomes cannot be quantified or reproduced in a consistent manner |
| | Clinical evidence is weak, although outcomes can be somewhat quantified and reproduced |
| | Clinical evidence is acceptable; outcomes can be somewhat quantified and reproduced, but variability prohibits formalization of evidence-based practices |
| | Clinical evidence is strong, but NOT consistent; facility is somewhat utilizing evidence-based practices |
| | Clinical evidence is strong and consistent; facility is effectively utilizing evidence-based practices |
| Practice guidelines | How strong are practice guidelines for treating indicated patients - and do they translate into clinical practice? |
| | No guidelines exist |
| | Guidelines are weak; they are general and require significant interpretation, resulting in poor application and high variability in the care continuum |
| | Guidelines are acceptable; formal, association-driven guidelines exist, but are not widely accepted, resulting in variability in the care continuum |
| | Guidelines are strong, but therapy is only mentioned as an option; guidelines are well accepted by healthcare professionals across the care continuum |
| | Guidelines are strong and therapy is recommended; guidelines are well accepted by healthcare professionals across the care continuum |
| Complication rates | Are procedure and post-procedure complication rates acceptable based on facility metrics or accepted norms for the procedure? |
| | Complication rates are unacceptable |
| | Complication rates are unacceptable, but improving |
| | Complication rates are acceptable for high-risk/high-benefit patients only Complication rates are neutral |
| | Complication rates are acceptable for MOST indicated patients |
| | Complication rates are acceptable for ALL indicated patients |
| Re-admissions | Are re-admission rates acceptable based on facility metrics or accepted norms for the procedure? |
| | Re-admission rates are unacceptable |
| | Re-admission rates are unacceptable, but improving |
| | Re-admission rates are acceptable for high-risk/high-benefit patients only Re-admission rates are neutral |
| | Re-admission rates are acceptable for MOST indicated patients |
| | Re-admission rates are acceptable for ALL indicated patients |
| Clinical outcomes measurement | How strong is the process for capturing and reporting meaningful outcomes for this procedure - to drive continuous improvement? |
| | No formal outcomes process exists; only measuring immediate results of the intervention |
| | No formal outcomes process exists, but measuring selected outcomes beyond immediate results of the intervention |
| | Outcomes process is in development or in its early stages |
| | Outcomes process is acceptable; but not fully utilized to drive improvement in processes and outcomes |
| | Outcomes process is strong; is being utilized to drive improvement in processes and outcomes |

As indicated above, user-selectable element 254 corresponds to the topic of hospital economics. Cells in the left column of the following table include example potential barriers related to the topic of hospital economics and cells in the right column of the following table include example multiple-choice barrier assessment questions related to the corresponding potential barrier.

| | |
|---|---|
| Reimbursement | Is the procedure optimally reimbursed for the facility? |
| | No reimbursement exists |
| | Reimbursement is not adequate and not being addressed |
| | Reimbursement is not adequate, but is being addressed |
| | Reimbursement is adequate; therapy is reimbursed and favorable changes to existing codes are in final external review |
| | Reimbursement is excellent; therapy is reimbursed within existing codes, resulting in optimal medical practice |
| Budget allocation | Are budgets sufficient for this therapy to support current volume and future growth? (Consider both payer and hospital.) |
| | No dedicated budgets for the therapy exist |
| | Dedicated budgets for the therapy are insufficient; very little is dedicated |
| | Dedicated budgets for the therapy are sufficient to support current therapy volume |
| | Dedicated budgets for the therapy are sufficient; but constrain growth |
| | Dedicated budgets for the therapy are excellent; they allow for healthy volume growth |
| Cost of care for procedure | Does the therapy have a positive impact on the cost of care based on relevant care metrics - and is the cost per procedure stable? |
| | Therapy has a negative impact on cost of care, with significant variability in the cost per procedure |
| | Therapy has a negative impact on cost of care, with some variability in the cost per procedure |
| | Therapy cost is similar to the current standard of care, with some variability in the cost per procedure |
| | Therapy has a marginally positive impact on cost of care, with minimal variability in the cost per procedure |
| | Therapy has a significantly positive impact on cost of care, with stable cost per procedure |
| Cost of care for follow-up | Do therapy follow-up costs have a positive impact on facility costs based on relevant care metrics - and are follow-up costs stable? |
| | Therapy follow-up costs have a significantly negative impact on facility costs, with significant variability |
| | Therapy follow-up costs have a negative impact on facility costs, with some variability |
| | Therapy follow-up costs are similar to the current standard of care, but with significant variability |
| | Therapy follow-up costs have a marginally positive impact on facility costs, with some variability |
| | Therapy follow-up costs have a significantly positive impact on facility costs, with very little variability |
| Physician economics | Are therapy economics favorable for the therapy-delivery physicians - relative to reimbursement levels and time allocation? |
| | Therapy economics are highly unfavorable; or the therapy is so new to the industry that no payment amount has been established |
| | Therapy economics are unfavorable; but proposed payment amounts or a favorable revision to existing payment has been proposed to the appropriate authorities |
| | Therapy economics are neutral; payment amounts are established, but need to be improved to support broad adoption |
| | Therapy economics are favorable; payment amounts are established and are sufficient to support broad adoption or physicians are salary-based and physician economics are not a barrier |
| | Therapy economics are highly favorable; payment amounts are established and are sufficient to support rapid adoption |
| Infrastructure investment | Does the therapy minimize the facility's need for capital investments - such as diagnostic infrastructure, IT upgrades or additional equipment - and technological expertise? |
| | Therapy significantly increases the need for capital investments and technological expertise to even sustain current therapy volume |
| | Therapy marginally increases the need for capital investments and technological expertise to sustain or increase volume |
| | Need for capital investments and technological expertise is neutral |
| | Therapy marginally decreases the need for capital investments to sustain or increase volume |
| | Therapy significantly decreases the need for capital investments to sustain or increase volume |
| Financial metrics | How strong are the facility's abilities to track and measure financial metrics by therapy? |
| | No financial metrics by therapy exist |
| | Financial metrics by therapy are extremely weak; but there is a desire to integrate more rigor |

Financial metrics by therapy are weak; new efforts have been recommended for tracking
Financial metrics by therapy are adequate; current implementation needs some minor revisions for tracking
Financial metrics by therapy are strong; the appropriate rigor has been applied at the therapy level As indicated above, user-selectable element 256 corresponds to the topic of capacity and efficiency. Cells in the left column of the following table include example potential barriers related to the topic of capacity and efficiency and cells in the right column of the following table include example multiple-choice barrier assessment questions related to the corresponding potential barrier.

| | |
|---|---|
| Diagnostic capacity | Does the facility have sufficient diagnostic capability - technology, clinician and nursing staff, and infrastructure - to effectively diagnose indicated patients? |
| | Extremely insufficient diagnostic capacity; limited or outdated technology and long waitlists |
| | Insufficient diagnostic capacity; limited or outdated technology, but few waitlists |
| | Sufficient diagnostic capacity to support current therapy volume only |
| | Sufficient diagnostic capacity to support future therapy growth |
| | Excellent diagnostic capacity; supports Standard of Care therapy volume |
| Patient screening and selection | Is there a standardized process in place within the healthcare system and are there clear, easily understood, measurable guidelines to routinely identify the appropriate patients for the therapy? |
| | Ill-defined diagnostic workup and inefficient screening |
| | Somewhat-defined diagnostic workup and efficient screening |
| | Well-defined diagnostic workup, but inefficient screening |
| | Well-defined diagnostic workup and efficient screening, but could be improved |
| | Fully-defined diagnostic workup and highly efficient screening |
| Treatment capacity | Is the facility's treatment capacity sufficient to support current therapy volume and future growth? |
| | Extremely insufficient capacity |
| | Insufficient capacity; some waitlists |
| | Sufficient capacity to support current therapy volume only |
| | Sufficient capacity to support future therapy growth |
| | Excellent capacity; supports Standard of Care therapy volume |
| Physician capacity and training level for procedure | Does the facility have sufficient physician capacity and training level to support the therapy? |
| | No physician capacity or training to support the therapy (beyond Key Opinion Leaders) |
| | Very limited physician capacity and training to support the therapy |
| | Sufficient physician capacity and training to support current therapy volume only |
| | Sufficient physician capacity and training to support future therapy growth |
| | Excellent physician capacity and training; supports Standard of Care therapy volume |
| Procedure standardization | Are the steps of the pre-op and operative procedures well defined and widely understood - with minimal variability among physicians? |
| | Ill-defined procedures and high variability among physicians |
| | Somewhat-defined procedures, but still high variability among physicians |
| | Well-defined procedures, with some variability among physicians |
| | Well-defined procedures, with minimal variability among physicians |
| | Fully-defined procedures, with no significant variability among physicians |
| Length of stay | Is the length of stay for indicated patients acceptable based on facility metrics or accepted norms for the procedure? |
| | Length of stay is unacceptable |
| | Length of stay is unacceptable, but improving |
| | Length of stay is acceptable for high- risk/high-benefit patients only |
| | Length of stay is acceptable for MOST indicated patients |
| | Length of stay is acceptable for ALL indicated patients |
| Follow-up capacity | Does the facility have sufficient capacity - technology, clinician and nursing staff, and infrastructure - to provide follow-up care? If not, is there a clear outside referral pathway? |
| | Insufficient follow-up capacity; outside referral pathway is unclear |
| | Insufficient follow-up capacity; but outside referral pathway exists |
| | Sufficient follow-up capacity to support current therapy volume only |

-continued

| | |
|---|---|
| | Sufficient follow-up capacity to support future therapy growth |
| | Excellent follow-up capacity; supports Standard of Care therapy volume |
| Follow-up care process | Is the follow-up care process well-defined, complete and flexible - and how strong are referral linkages for follow-up care? |
| | No follow-up process and no linkages between therapy-delivery physicians and follow-up physicians |
| | Ill-defined follow-up care process and weak follow-up linkages |
| | Somewhat-defined follow-up care process and weak follow-up linkages; supports current therapy volume only |
| | Well-defined follow-up care process and strong follow-up linkages; supports future therapy growth |
| | Fully-defined follow-up care process and extremely strong follow-up linkages |

As indicated above, user-selectable element 258 corresponds to the topic of patient pathways. Cells in the left column of the following table include example potential barriers related to the topic of patient pathways and cells in the right column of the following table include example multiple-choice barrier assessment questions related to the corresponding potential barrier.

| | |
|---|---|
| Patient concentration | Where are the indicated patients within your healthcare system? |
| | Majority of indicated patients not entering the healthcare system |
| | Indicated patients are distributed with no specialty having >25% |
| | >25% of indicated patients are with a specialty group not referring |
| | >25% of indicated patients are with a current referrer OR >10% are in the care of the prescriber or therapy specialist |
| | >25% of indicated patients are in the care of the prescriber or therapy specialist |
| Referrer motivation | Are referring physicians aware of the target therapy and motivated to refer patients? |
| | No; referring physicians are unaware of the therapy and/or unmotivated to refer patients |
| | Referring physicians are aware of the therapy but unmotivated to refer patients; because it would require significant changes in their practice |
| | Referring physicians are aware of the therapy and neutral about referring patients |
| | Referring physicians are aware of the therapy and motivated to refer patients; but some barriers exist to improving referral patterns |
| | Referring physicians are very familiar with the therapy and highly motivated to refer patients |
| Community referral linkages | How strong are referral linkages for indicated patients within the community (service area)? |
| | No linkages exist in the community between referrers and therapy-delivery physicians |
| | Referral linkages are weak; some exist, but there are incentives or bias to not refer |
| | Referral linkages are acceptable; some exist, but are not well developed and there are few incentives |
| | Referral linkages are acceptable, with champions trying to improve them |
| | Referral linkages are strong; incentives exist for both parties with comfortable two-way communication regarding the patient |
| Facility referral linkages | How strong are referral linkages for indicated patients within the facility? |
| | No linkages exist in the facility between referrers and therapy-delivery physicians |
| | Referral linkages are weak; incentives are not aligned among departments |
| | Referral linkages are acceptable; some exist, but are not well developed |
| | Referral linkages are acceptable, with champions trying to improve them |
| | Referral linkages are strong; incentives exist for both parties with comfortable two-way communication regarding the patient |
| Prescriber and therapy-delivery physician motivation | Are prescribing and/or therapy-delivery physicians aware of the target therapy and motivated to prescribe or perform the procedure? |
| | No; therapy is new, outside the comfort zone, and requires many changes in their practice |
| | No, but would NOT require much change in their practice |
| | They are aware of the therapy, but there are few incentives to prescribe or perform the procedure |
| | They are familiar with the therapy and have some incentives to prescribe or perform the procedure |
| | They are very familiar with the therapy and have many incentives to prescribe or perform the procedure |

| | |
|---|---|
| Standardization of care pathway | Is there strong alignment around and minimal variability in the care pathway for this therapy across departments?<br>No alignment around and high variability in care pathway across departments<br>No alignment, but minimal variability in care pathway<br>Some alignment and minimal variability in care pathway<br>Strong alignment and minimal variability in care pathway<br>Strong alignment and no variability in care pathway |

As indicated above, user-selectable element 260 corresponds to the topic of patient experience. Cells in the left column of the following table include example potential barriers related to the topic of patient experience and cells in the right column of the following table include example multiple-choice barrier assessment questions related to the corresponding potential barrier.

| | |
|---|---|
| Facility reputation | Is the facility's reputation and competitive advantage strong - can it attract patients and top talent within its service area?<br>Facility's reputation is weak; significant improvements needed<br>Facility's reputation is weak, but improving<br>Facility's reputation is neutral<br>Facility's reputation is strong, but has no clear competitive advantage<br>Facility is considered a Center of Excellence and has a clear competitive advantage |
| Patient education and resources | How strong is patient education - regarding introduction to the therapy and any ongoing support that may be required?<br>Patient introduction or ongoing support does not exist<br>Both patient introduction and ongoing support are weak<br>Patient introduction is moderate, but ongoing support is weak<br>Patient introduction is strong, but ongoing support is moderate<br>Both patient introduction and ongoing support are strong |
| Patient experience measurement | How strong are the facility's abilities to track and measure patient experience metrics - and use them to improve service?<br>The patient experience is not yet defined and no metrics exist<br>The patient experience is defined, but no metrics exist<br>Patient experience metrics are weak, but are being developed<br>Patient experience metrics are strong, but are not being used to improve service<br>Patient experience metrics are strong, and are being used to improve service |
| Patient satisfaction | Does the therapy increase overall patient satisfaction - and does the facility offer staff incentives to improve patient satisfaction?<br>Therapy decreases patient satisfaction and there are no incentives to improve satisfaction<br>Therapy has potential to decrease patient satisfaction and there are few incentives to improve satisfaction<br>Therapy does not impact patient satisfaction<br>Therapy increases patient satisfaction, but there are very few incentives to improve satisfaction<br>Therapy significantly increases patient satisfaction and there sufficient incentives to continually improve satisfaction |

Thus, as indicated in the example barrier assessment questions listed above, the barrier assessment questions include barrier assessment questions related to at least one of: clinical evidence, practice guidelines, complication rates, re-admissions, clinical outcomes measurements, reimbursement, budget allocation, cost of care for the medical therapy, cost of care for follow up for the medical therapy, physician economics, infrastructure investment, financial metrics, diagnostic capacity, patient screening and selection, treatment capacity, physician capacity and training level for the medical therapy, procedure standardization, length of stay of patients for the medical therapy, follow-up care capacity for the medical therapy, definition of a follow-up care process for the medical therapy, patient concentration, referrer motivation regarding the medical therapy, community referral linkages regarding the medical therapy, facility referral linkages regarding the medical therapy, prescriber and therapy-delivery physician motivation regarding the medical therapy, standardization of care pathway for the medical therapy, facility reputation of the healthcare provider, patient education and resources, patient experience measurement, and patient satisfaction.

In any embodiment of the first through seventh aspects of the invention, some of the data listed in the tables above can be automatically obtained by the system. For example, data indicative of complication rates, readmissions, and length of stay can be obtained directly from the facility records. In such cases, the system can use the quantitative values for these indicators as opposed to the more subjective qualitative values.

In any embodiment of the first through seventh aspects of the invention, the barriers may be identified using a factor set that has been created through the creation and subsequent evaluation of a variety of factors that influence the annual adoption rate of a therapy, diagnostic or a solution in the market. Factors have been created by experts world-wide and may be pared to relevant subsets by statistical modeling. In any embodiment of the first through seventh aspects of the invention, the barrier groupings are driven by experience in sequencing those factors in order to expedite annual adoption rate.

In any embodiment of the first through seventh aspects of the invention, the system can provide an initial barrier prioritization rank order based on correlation coefficients calculated as described herein. The initial barrier prioritization rank order can be a listing of potential barriers to patients receiving a medical therapy in an order based on the degree to which each barrier affects the number of times a healthcare provider is providing the medical therapy. After receiving user input concerning the potential barriers as described herein, the system can determine a subsequent barrier prioritization rank order, wherein the barriers are prioritized based on an estimated effect each barrier is actually having on the number of times the healthcare provider is providing the medical therapy. The subsequent barrier prioritization rank order can be based on both the correlation coefficients and quantitative values corresponding to barrier scores as described herein.

In any embodiment of the first through seventh aspects of the invention, barriers that are associated may be grouped together by category. For example, the potential barriers of Clinical Evidence, Practice Guidelines, Complication Rates, Readmissions, Clinical Outcomes Measurement may be categorized together as barriers relating to "clinical excellence." In any embodiment of the first through seventh aspects of the invention, barriers that are grouped together may be presented together in the initial or subsequent barrier prioritization rank order. For example, if "clinical evidence" is determined to have the largest impact on the number of times a healthcare provider will provide a medical therapy by having the highest correlation coefficient, then all of the barriers relating to clinical excellence, in which clinical evidence is categorized, may be shown together in the initial or subsequent barrier prioritization rank order, even if the calculated correlation coefficient for one or more of the individual barriers is lower than the correlation coefficient for an individual barrier that is not part of the clinical evidence grouping.

Based on initial studies on the effect of barriers on the number of times a healthcare provider will provide a medical therapy, an initial barrier prioritization rank order may be as follows: Clinical Evidence, Practice Guidelines, Complication Rates, Readmissions, Clinical Outcomes Measurement, Reimbursement, Budget Availability, Cost of Care for Procedure, Cost of Care Follow-up, Physician Economics, Infrastructure Investment, Financial Metrics, Diagnostic Capacity, Patient Screening Selection, Treatment Capacity, Clinician Capacity in Skill, Procedure Standardization, Length of Stay, Follow-up Capacity, Follow-up Care Process, Patient Concentration, Referrer Motivation, Community Referral Links, Interdepartment Patient Pathways, Prescriber Motivation, Standardization of Care, Hospital Reputation, Patient Education and Resources, Patient. Experience Measurement, and Patient Satisfaction. This initial barrier prioritization rank order is based on determinations that clinical evidence has the highest impact on the number of times a healthcare provider provides a medical therapy as determined by the correlation coefficients for each of the barriers. As such, all of the barriers associated with the category of "clinical excellence" are prioritized together. The clinical excellence category is followed by barriers associated with hospital economics, barriers associated with capacity and efficiency, barriers associated with patient pathways, and barriers associated with patient experience as described herein. In any embodiment of the first through seventh aspects of the invention, the initial barrier prioritization rank order can instead be based on the individual barrier correlation coefficients instead of presented as groups of barriers.

FIG. 9 is a conceptual diagram showing an example barrier assessment interface 300, in accordance with one or more techniques of this disclosure. In the example of FIG. 9, there are thirty potential barriers to patients receiving the medical therapy from the hospital. The potential barriers are categorized by topic. Data processing unit 16 may determine, based on the answers to the barrier assessment questions described above with regard to FIG. 8, a score for each of the barriers.

Data processing unit 16 may determine the score for a barrier in various ways. In one example of the first through seventh aspects of the invention, a scaled response to a multiple choice question can be used to determine the barrier score. In any embodiment of the first through seventh aspects of the invention, the responses to the multiple choice questions can be scaled using a Likert scale. A Likert scale is a process, known in the art, for scaling responses to multiple choice questions into quantitative data. One skilled in the art will understand that any method of quantifying the responses to multiple choice questions is contemplated by the first through seventh aspects of the invention. For each respective barrier assessment question described above, each of the potential answers to the respective barrier assessment question is assigned a scaled score. For instance, in this example, the first potential answer to the respective barrier assessment question may be assigned a score of 1, the second potential answer to the respective barrier assessment question may be assigned a score of 2, the third potential answer to the respective barrier assessment question may be assigned a score of 3, and so on. In this example, data processing unit 16 may determine that the score for the potential barrier associated with the respective barrier assessment question is equal to the score assigned to the selected potential answer for the respective barrier assessment question. In any embodiment of the first through seventh aspects of the invention, there can be a one to one relationship between assessment questions and a barrier. That is, for each potential barrier, a single question can be provided. In any embodiment of the first through seventh aspects of the invention, there may be multiple barrier assessment questions associated with the same potential barrier and data processing unit 16 may perform one or more mathematical operations to determine the scores for potential barriers based on answers selected for the barrier assessment questions associated with the potential barrier.

As shown in barrier assessment interface 300 of FIG. 9, the scores for each of the potential barriers for each of the topics are represented as bar graphs. Larger bars in the bar graphs may correspond to potential barriers with greater scores and smaller bars in the bar graphs may correspond to potential barriers with lesser scores. As described herein, potential barriers with greater scores may represent barriers that have been more largely overcome. In any embodiment of the first through seventh aspects of the invention, however, potential barriers with greater scores may represent barriers that have not been as largely overcome. Hence, the bar graphs shown in barrier assessment interface 300 may help the hospital to visualize which of the potential barriers are most likely to prevent patients from accessing the medical therapy from the hospital. In other words, the bar graphs shown in barrier assessment interface 300 may indicate the relative severity of the barriers. In this disclosure, a first barrier may be considered to be more severe than a second barrier if the first barrier is more responsible for patients not receiving the medical therapy from the healthcare provider than the second barrier. In any embodiment of the first through seventh aspects of the invention, the data processing unit 16 may generate and output displays other than the graphs described. One skilled in the art will understand that the output may be alternatively displayed as a text-based listing of the same data.

In any embodiment of the first through seventh aspects of the invention, larger bars in the bar graphs may correspond to potential barriers with lesser scores and smaller bars in the bar graphs may correspond to potential barriers with greater scores. In any embodiment of the first through seventh aspects of the invention, potential barriers with lesser scores may be more responsible for preventing patients from accessing the medical therapy from the hospital than potential barriers with greater scores. In any embodiment of the first through seventh aspects of the invention, potential barriers with lesser scores may be less responsible for preventing patients from accessing the medical therapy from the hospital than potential barriers with greater scores.

In this way, data processing unit 16 may receive indications of user input indicating selected answers to multiple-choice questions regarding one or more barriers (e.g., the barrier assessment questions described above) to patients receiving a medical therapy from a healthcare provider. Each of the answers to the multiple-choice questions may correspond to a quantitative value. Furthermore, as part of generating data targeted to facilitating the decision-making process, data processing unit 16 may generate, based on the quantitative values corresponding to the selected answers, one or more diagrams (e.g., the bar graphs of FIG. 9) indicating relative severity of the one or more barriers in preventing the patients from receiving the medical therapy from the healthcare provider.

FIG. 10 is a conceptual diagram showing an example barrier prioritization interface 350, in accordance with one or more techniques of this disclosure. In the example of FIG. 10, barrier prioritization interface 350 comprises a table having rows that correspond to particular barriers. In any embodiment of the first through seventh aspects of the invention, the particular barriers shown in barrier prioritization interface 350 have scores that are beyond a particular threshold. For instance, in any embodiment of the first through seventh aspects of the invention where potential barriers with greater scores are more responsible for preventing patients from accessing the medical therapy from the hospital than potential barriers with lesser scores and the scores for potential barriers range from 1 to 5, barrier prioritization interface 350 may include rows that correspond to potential barriers having scores greater than or equal to 4. In any embodiment of the first through seventh aspects of the invention where potential barriers with greater scores are less responsible for preventing patients from accessing the medical therapy from the hospital than potential barriers with lesser scores and the scores for potential barriers range from 1 to 5, barrier prioritization interface 350 may include rows that correspond to potential barriers having scores less than or equal to 2.

For each respective barrier indicated in barrier prioritization interface 350, barrier prioritization interface 350 includes a cell for entry of a description of the respective barrier (i.e., a barrier description). Furthermore, for each respective barrier indicated in barrier prioritization interface 350, barrier prioritization interface 350 includes a cell for entry of a score correlated with the hospital's ability to impact the respective barrier. In addition, for each respective barrier indicated in barrier prioritization interface 350, barrier prioritization interface 350 includes a cell for entry of a score correlated with the impact that reducing the respective barrier would have on increasing the number of times the hospital provides the medical therapy (i.e., the impact on success). In the example of FIG. 10, the score correlated with the hospital's ability to impact the respective barrier and the score correlated with the impact on success ranges from 1 to 10. In any embodiment of the first through seventh aspects of the invention, these scores may have various other ranges. Furthermore, for each respective barrier indicated in barrier prioritization interface 350, barrier prioritization interface 350 includes a cell for entry of notes regarding the respective barrier. In addition, for each respective barrier indicated in barrier prioritization interface 350, barrier prioritization interface 350 includes a cell containing a checkbox for indicating whether the hospital considers the respective barrier to be a priority. In the example of FIG. 10, the user has inputted a barrier description of "Limited budgets for CRT" as a barrier description for the "budget availability" barrier, "4" as an ability to impact score for the "budget availability" barrier, and "9" as an impact on success score for the "budget availability" barrier.

Data processing unit 16 may receive indications of user input into cells of barrier prioritization interface 350, and, in response, may output corresponding data in the cells of barrier prioritization interface 350. Furthermore, in response to receiving the indications of user input into cells of barrier prioritization interface 350, data processing unit 16 may store the data indicated by the user input for subsequent use.

In the example of FIG. 10, barrier prioritization interface 350 includes a button 352. In response to receiving an indication of a user selection of button 352, data processing unit 16 may output barrier prioritization interface 350 for display such that barrier prioritization interface 350 includes one or more additional rows for one or more additional barriers.

FIG. 11 is a conceptual diagram illustrating an example barrier prioritization matrix 400, in accordance with one or more techniques of this disclosure. Barrier prioritization matrix 400 includes bubbles that correspond to particular barriers. In any embodiment of the first through seventh aspects of the invention, the bubbles correspond to the barriers indicated in barrier prioritization interface 350. For each respective bubble in barrier prioritization matrix 400, the position of the respective bubble within barrier prioritization matrix 400 correlates with the hospital's ability to impact the barrier corresponding to the respective bubble and the estimated impact on success for reducing the barrier corresponding to the respective bubble. For instance, in the example of FIG. 11, bubbles corresponding to barriers that the hospital has a high ability to impact may be further right than bubbles corresponding to barriers that the hospital has a low ability to impact. Moreover, in the example of FIG. 11, bubbles corresponding to barriers whose reduction would have a high impact on success may be further up than bubbles corresponding to barriers whose reduction would have a relatively low impact on success.

In any embodiment of the first through seventh aspects of the invention, the data processing unit 16 may be configured to allow the user to provide an indication of barrier priority. The barrier prioritization matrix, described herein, can include these user selected priority barriers. This allows the user to determine which of the barriers determined in the initial and subsequent barrier prioritization rank orders are shown in the barrier prioritization matrix, using the first barrier prioritization rank order and the second barrier prioritization rank order.

In any embodiment of the first through seventh aspects of the invention, the relative impact on success of the barriers in the barrier prioritization matrix shown in FIG. 11 can be based on calculated correlation coefficients as described herein. In any embodiment, the correlation coefficient can represent the effect of a change in a barrier score for a particular barrier on the amount of times a health care provider will provide a medical therapy. The correlation coefficients can be obtained from statistics obtained for each of the barriers or can be determined by the processor of the invention using data entered into the system. The impact on success ranking in the barrier prioritization matrix can be based on the effect reducing each of the barriers will have on the number of times the healthcare provider will provide the therapy as determined by the calculated correlation coefficients. That is, the barrier reductions that will have the largest impact on success can be listed near the top of the diagram shown in FIG. 11. In any embodiment of the first through seventh aspects of the invention, barriers with a high barrier score can be excluded from the barrier prioritization matrix. That is, barriers that have been largely eliminated need not be included. One skilled in the art will understand that the cut-off point for excluding a barrier can be set at any score. For example, if the barrier scores are between 1 and 5, with a five indicating that the barrier has been completely eliminated as described herein, barriers with a score of 4 or above can be excluded from the barrier prioritization matrix. One skilled in the art will understand that the barrier scores can be determined on any scale, and need not be from 1 to 5. One skilled in the art will also understand that a lower number for a barrier score could indicate that the barrier has been reduced, instead of a higher number as in the example. The cut off point for exclusion of a barrier from the barrier prioritization matrix can be set at any number in any embodiment of the first through seventh aspects of the invention.

Because of the positions of the bubbles within barrier prioritization matrix 400, the hospital may be able to understand easily which barriers the hospital has a high ability to impact and those whose reduction would have the greatest impact on increasing the number of times the hospital provides the medical procedure. The hospital may choose to prioritize the barriers that the hospital has a high ability to impact and those whose reduction would have the greatest impact on increasing the number of times the hospital provides the medical procedure. For instance, in the example of FIG. 11, the hospital may choose to prioritize the community referral links barrier and the clinical outcome measurement barrier for reduction.

In any embodiment of the first through seventh aspects of the invention, particular bubbles in barrier prioritization matrix 400 may be visually differentiated from other bubbles in barrier prioritization matrix 400 depending on whether the priority boxes for the corresponding barriers in barrier prioritization interface 350 of FIG. 10 are checked. For example, if the priority box for the "clinical evidence" barrier is checked in barrier prioritization interface 350, the bubble corresponding to the "clinical evidence" barrier in barrier prioritization matrix 400 may be filled with the color blue while bubbles corresponding to barriers whose priority boxes are not checked may be filled with the color white. In any embodiment of the first through seventh aspects of the invention, the data processing unit 16 may generate and output displays other than the charts described. One skilled in the art will understand that the output may be alternatively displayed as a text-based listing of the same data.

In any embodiment of the first through seventh aspects of the invention, data processing unit 16 may output barrier prioritization interface 350 again after outputting barrier prioritization matrix 400 for display. This may afford the user another opportunity to change the data entered in barrier prioritization interface 350. For instance, this may afford the user the opportunity to change which priority boxes are checked based on a review of barrier prioritization matrix 400.

As indicated elsewhere in this disclosure, the decision-making process may comprise prioritizing the one or more barriers. In accordance with one or more techniques of this disclosure, data processing unit 16 may receive indications of user input indicating first quantitative data estimating an ability of a healthcare provider to reduce at least a subset of the one or more barriers and second quantitative data estimating an impact of efforts by the healthcare provider to reduce the subset of the one or more barriers in increasing how many times the healthcare provider provides the medical therapy (e.g., impact on success scores and ability to impact scores). Furthermore, as part of generating data targeted to facilitating the decision-making process, data processing unit 16 may generate, based on the first quantitative data and the second quantitative data, a diagram (e.g., barrier prioritization matrix 400) that enables a comparison of barriers in the subset of the one or more barriers. In any embodiment of the first through seventh aspects of the invention (such as barrier prioritization matrix 400), the diagram comprises, for each respective barrier in the subset, a bubble corresponding to the respective barrier, wherein the bubble corresponding to the respective barrier is positioned in the diagram according to an ability of the healthcare provider to reduce the respective barrier and an estimated impact of efforts by the healthcare provider to reduce the respective barrier in increasing how many times the healthcare provider provides the medical therapy.

In any embodiment of the first through seventh aspects of the invention, the data processing unit 16 may automatically estimate the quantitative data estimating the ability of a healthcare provider to reduce at least a subset of the one or more barriers. Based on previous results from barrier reduction efforts with similar or different therapies, the data processing unit 16 can determine how effective efforts are estimated to be at reducing specific barriers. For example, if the healthcare provider has previously had success reducing barriers associated with physician economics, data processing unit 16 may provide a quantitative score indicating a high ability to reduce the barrier. If the healthcare provider has not had success in reducing a particular barrier, then data processing unit 16 may provide a quantitative score indicating a lower ability to reduce the barrier.

In any embodiment of the first through seventh aspects of the invention, the data processing unit 16 may automatically estimate the quantitative data estimating an impact of efforts by the healthcare provider to reduce the subset of the one or more barriers in increasing how many times the healthcare provider provides the medical therapy. For example, if previous barrier reduction efforts were successful in reducing a particular barrier with a different therapy, data processing unit 16 can determine the quantitative effect of that reduction on the number of times the healthcare provider provided the therapy. Based on the effect of barrier reduction had on the number of times the healthcare provider provided other therapies, data processing unit 16 can estimate the estimated effect of reducing the same barriers with a new medical therapy.

In any embodiment of the first through seventh aspects of the invention, the data processing unit 16 can comprise a memory component. The memory component can receive data indicating a change in the barrier scores for a medical treatment as described herein, and the change in the amount of times the healthcare provider has provided a treatment after the change in the barrier scores. The data processing unit 16 can then determine the estimated effects of reducing the same barriers on different medical therapies. The effects of barrier reduction on the amount of times a therapy is performed can be expressed as a correlation coefficient. The correlation coefficient for each barrier gives the estimated effect of a reduction of that barrier on the amount of times the therapy will be performed by the healthcare provider. Any statistical calculations performed by the data processing unit 16 in order to determine the correlation coefficients are within the scope of the first through seventh aspects of the invention, including, but not limited to, stepwise regression, stepwise multiple regression, R-square, Akaike information criterion, Bayesian information criterion, and Mallows's Cp. One skilled in the art will understand how to calculate correlation coefficients from actual data corresponding to changes in barrier scores and the effect of those changes on the amount of times the therapy is performed. As the number of data points entered into data processing unit 16 increases, the accuracy of the statistical calculations will increase, allowing more accurate calculation of the correlation coefficients for each barrier.

Figure 17:
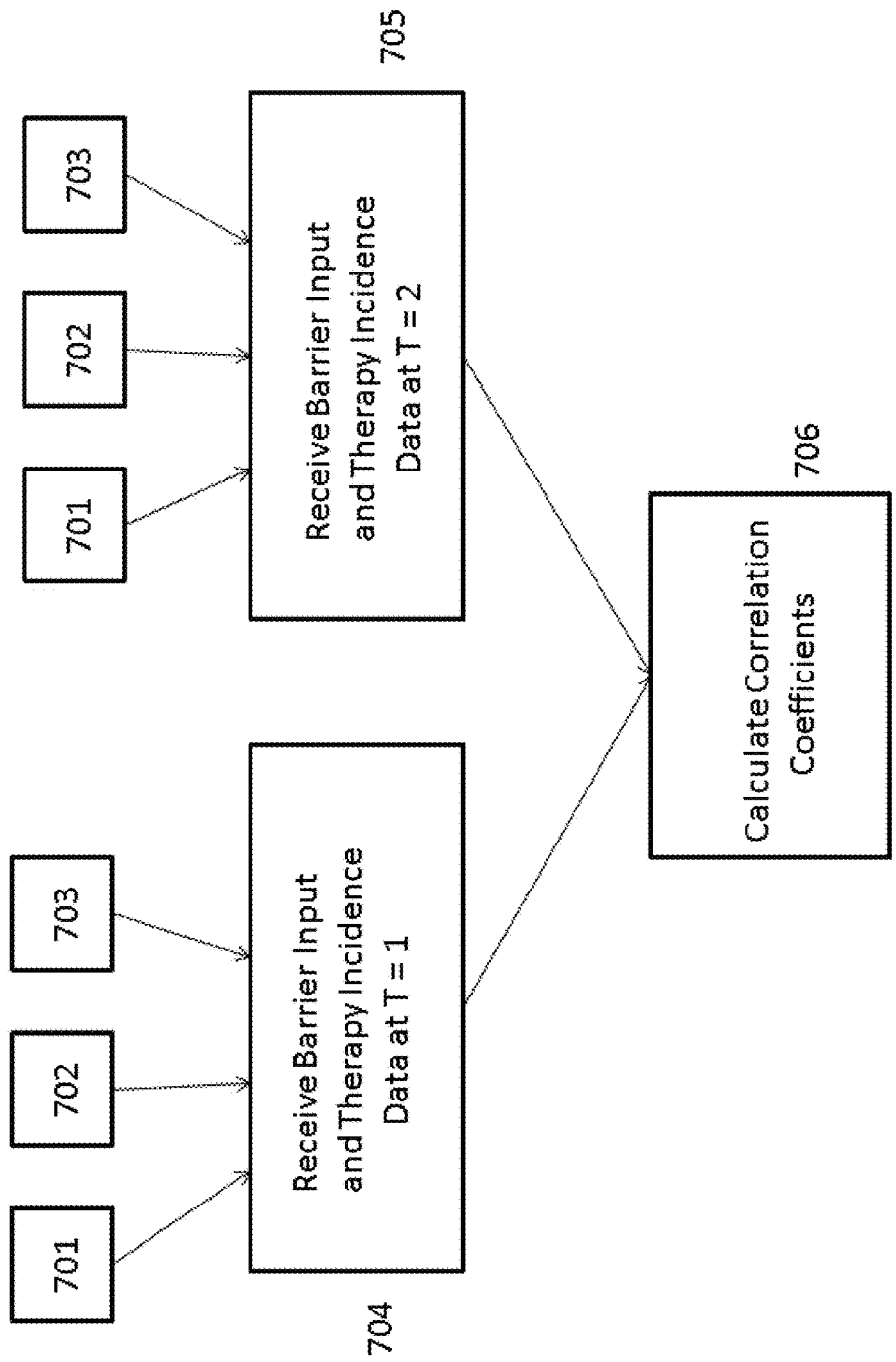
FIG. 17 is a flowchart illustrating an example of the steps carried out to determine correlation coefficients for barriers to therapy.

The steps that can be taken to calculate the correlation coefficients for the barriers are shown in FIG. 17. Barrier scores can be received by the system for multiple healthcare providers, therapies or geographic locations 701, 702, and 703. One skilled in the art will understand that although three sources of information are shown in FIG. 17, more data can be received from more than three sources. As the number of sources of data increase, the accuracy of the calculated correlation coefficients will also increase. The barrier scores and incidence of therapy provided are received by the system in step 704 at a time labeled T=1. The incidence of therapy provided refers to the amount of times the healthcare provider has provided the therapy in a specified time period. The barrier scores and incidence of therapy provided can also be received by the system from the same sources 701, 702 and 703 at a later time, labeled T=2 in step 705. Based on the changes in the number of times the healthcare provider provides the therapy with respect to the changes in the various barrier scores, the correlation between barriers and the number of times the healthcare provider provides the therapy can be calculated as described herein at step 706. One skilled in the art will understand that the barrier scores and incidence of therapy can be obtained more than two times. Obtaining the barrier scores and incidence of therapy can be done 2, 3, 4, 5, 6 or more times. One skilled in the art will understand that the more data collected, the more accurate the calculation of the correlation coefficients will be. Further, some barriers may be time dependent, or dependent on the number of treatments performed. As such, collected data multiple times enables the system to determine the effectiveness of barrier reduction over longer time periods and over changes to the number of times the healthcare provider provides the therapy.

In any embodiment of the first through seventh aspects of the invention, the list of barriers and questions for the users can be changed. As more data is obtained, certain barriers may have correlation coefficients that are so low that the barriers have little or no impact on the number of times the healthcare provider provides the therapy. The system can be configured so as to eliminate questions that have been consistently shown to have little or no impact on the number of times the healthcare provider provides the therapy. As more data is obtained, the list of barriers that do have an effect on the number of times that the healthcare provider provides the therapy can be reassessed and revalidated.

In any embodiment of the first through seventh aspects of the invention, barrier weights may be determined based on the correlation coefficients. Barrier weights refer to the estimated impact of the barriers in preventing patients from receiving a medical therapy from a healthcare provider. The correlation coefficients can be scaled, providing barrier weights, to allow for more detailed analysis of the reasons patients are not obtaining a medical therapy from the healthcare provider. By scaling barriers using barrier weights based on calculated correlation coefficients, the relative severity of each of the barriers can be determined.

The data processing unit 16 can also determine the change in correlation coefficients for each barrier based on the starting barrier score as described herein. The correlation coefficient for a specific barrier may not be constant throughout development of a medical therapy. For instance, at a time when most barriers are high, that is when most of the answers to the questions listed herein are negative, certain barrier reductions may have a larger impact on the amount of times the healthcare provider provides the medical therapy than the same barrier reduction when most of the other barriers are low. For example, if there are a significant amount of barriers present, a reduction in a barrier score for physician economics may not correspond strongly to an increase in the number of times the healthcare provider provides the therapy. However, when other barriers have been reduced, and the overall barrier score is low, then a reduction in a physician economics barrier may have a larger effect on the number of times the health care provider provides the therapy. One skilled in the art will understand that as the amount of data saved in the data processing unit increases, a number of statistical calculations can be performed to determine the change in correlation coefficients based on the barrier scores for other barriers. In any embodiment of the first through seventh aspects of the invention, the statistical calculations can be performed each time new results are entered into the data processing unit, allowing for a constantly updated correlation coefficient for each barrier. In any embodiment of the first through seventh aspects of the invention, the statistical calculations can be updated periodically, such as weekly, monthly or yearly.

Figure 18:
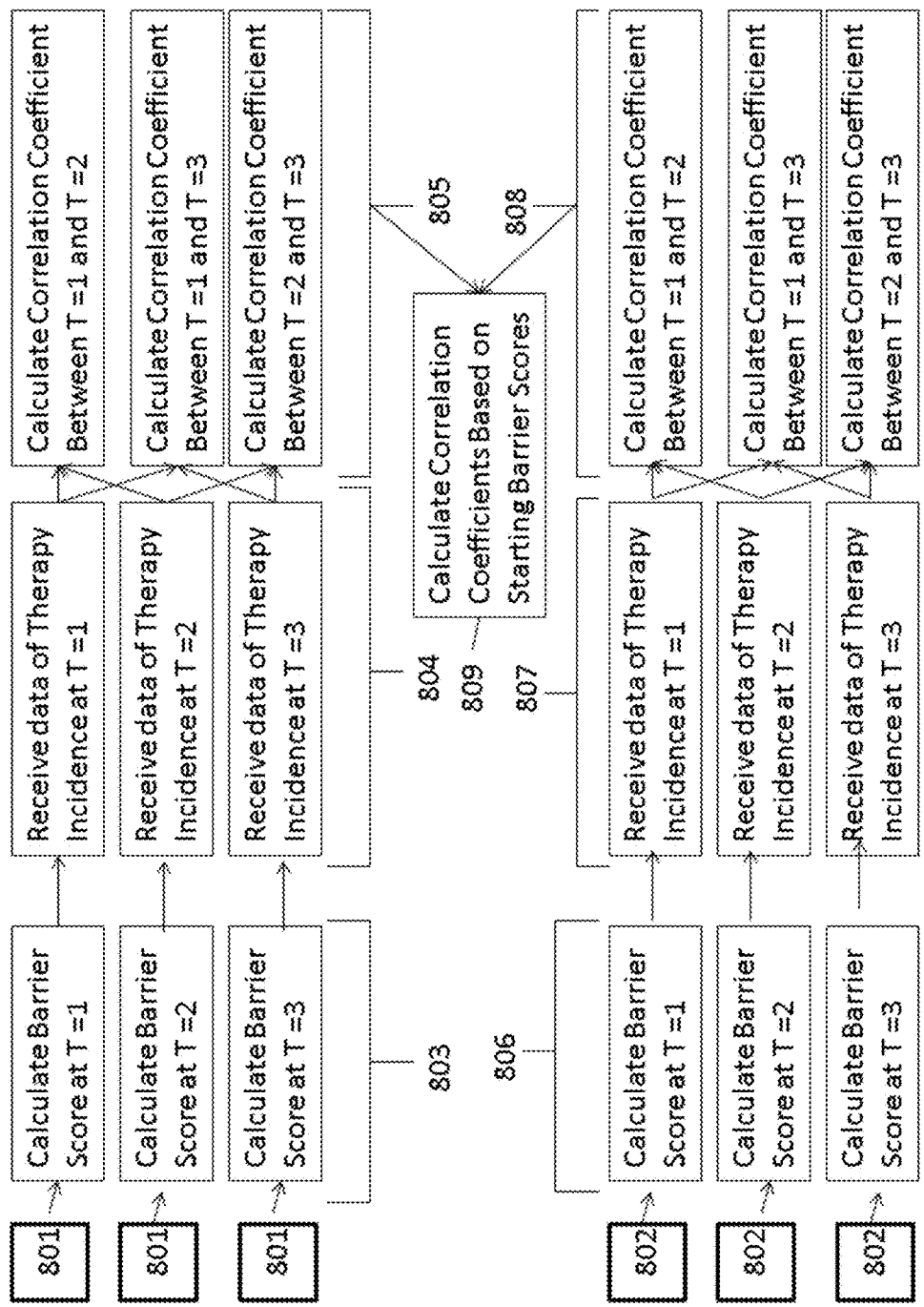
FIG. 18 is a flowchart illustrating an example of the steps carried out to determine the change in correlation coefficients with respect to barrier score.

A method of determining the change in barrier scores with respect to the starting barrier scores is shown in FIG. 18. The system can calculate the barrier score for a healthcare provider 801 at time T=1, T=2 and T=3 in step 803. Although only three times are shown in FIG. 18, one skilled in the art will understand that the data can be received any number of times. The system can also receive data of the incidence of therapy provided at each time in step 804. In step 805, the system can calculate correlation coefficients based on the data received in steps 803 and 804 corresponding to the effect of reducing barriers on the number of times the healthcare providers provides the therapy for each time interval. In FIG. 18, the system is shown calculating correlation coefficients for the healthcare provider between times T=1 and T=2, between times T=1 and T=3, and between times T=1 and T=2. The same data can be received for a second healthcare provider, or a second therapy 802. Calculation of scores for each barrier can be determined in step 806 at each time interval. Incidence of therapy provided can be received at each time interval in step 807. Correlation coefficients can be calculated for each possible time interval in step 808. Although two healthcare providers, medical therapies or geographic locations are shown in FIG. 18, one skilled in the art will understand that the calculations will be more accurate with more sources of data. Based on the difference in correlation coefficients with respect to starting barrier scores calculated in steps 805 and 808, the system can calculate the effect of the starting barrier score on the correlation coefficient for each barrier in step 809.

Figure 19:
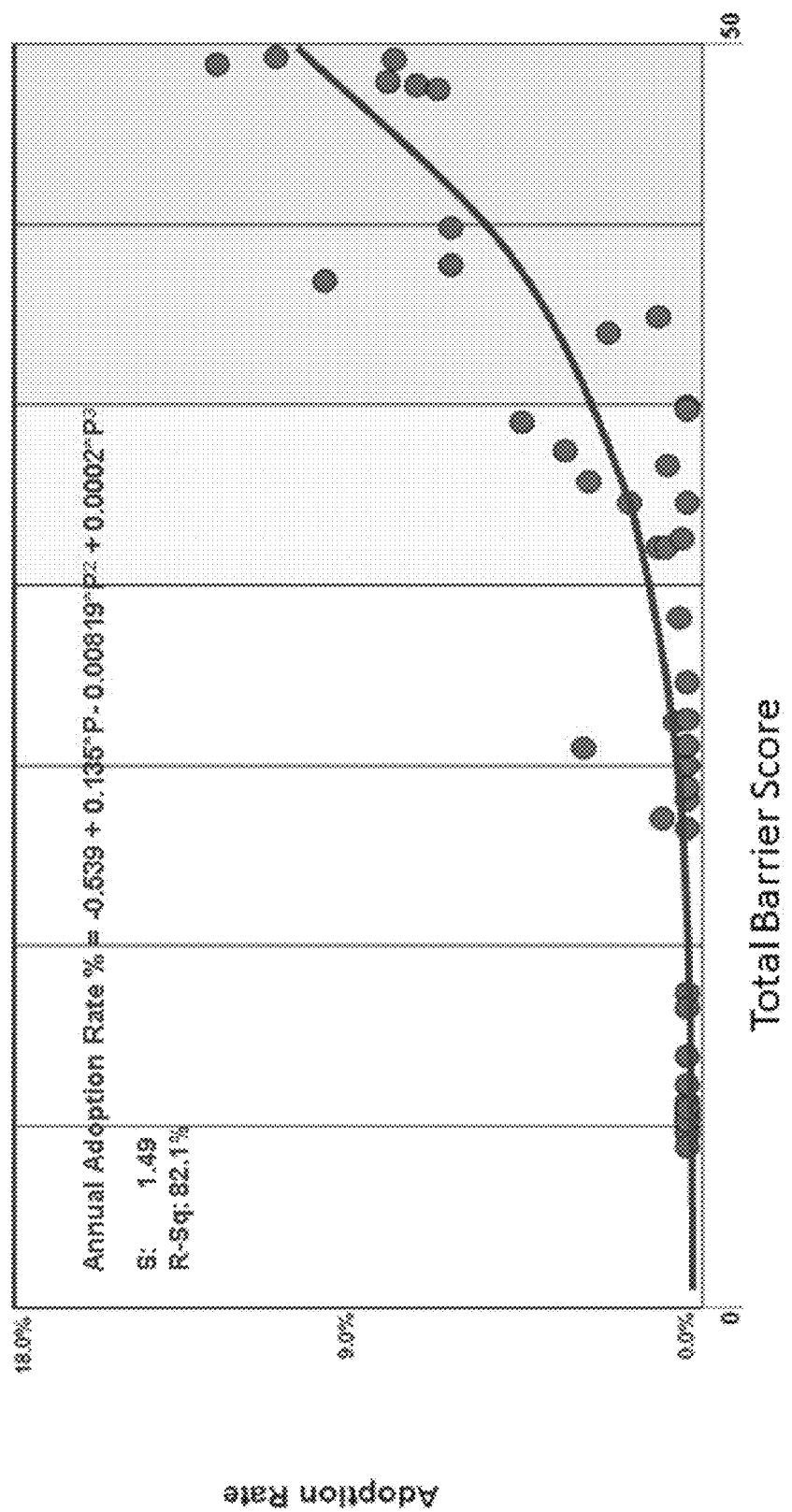
FIG. 19 is a graph illustrating the effect of barrier reduction on the annual adoption rate of a medical therapy.

FIG. 19 is a sample chart showing the effect of the total barrier score on the annual adoption rate. The annual adoption rate in FIG. 19 is the absolute penetration of the medical therapy of the patient pool. The annual adoption rate is defined in FIG. 19 as the number of times the healthcare provider provides the therapy divided by the number of years times 1+the penetration of incidence. The x-axis in FIG. 19 is the total barrier score. The lower that the barriers to patients receiving the medical therapy are, the further to the right on the graph. The y-axis is the annual adoption rate as explained above. As shown in FIG. 19, as the barriers are reduced, the annual adoption rate increases. For the data used in FIG. 19, a best fit line was obtained having an equation Annual Adoption Rate=$-0.539+0.135*P-0.00819*P^2+0.0002*P^3$, where P is the barrier score. From this equation, one can calculate the estimated effect of reducing barriers on the incidence of therapy. One skilled in the art will understand that as more data is collected and more data points inserted into the chart, the derived equation may change.

In any embodiment of the first through seventh aspects of the invention, the data processing unit 16 may determine the change in correlation coefficients for each barrier based on the opportunity sizing data obtained as described herein. Certain barriers may have a larger impact at a time when the healthcare provider is providing a medical therapy much less often that the healthcare provider could provide the medical therapy based on the prevalence of the medical condition and other opportunity sizing data described herein. As the healthcare provider moves closer to the opportunity size in terms of how often the healthcare provider provides the medical therapy, other barriers may have a larger effect on the amount of times the healthcare provider provides the medical therapy. In any embodiment of the first through seventh aspects of the invention, the statistical calculations can be performed each time new results are entered into the data processing unit concerning the opportunity size and number of times the healthcare provider provides the medical therapy, allowing for a constantly updated correlation coefficient for each barrier. In any embodiment of the first through seventh aspects of the invention, the statistical calculations can be updated periodically, such as weekly, monthly or yearly.

FIG. 12 is a conceptual diagram illustrating an example action planning interface 450, in accordance with one or more techniques of this disclosure. Action planning interface 450 may include a primary row for each barrier whose priority box is checked in barrier prioritization interface 350. For ease of explanation, FIG. 12 only shows a single primary row. Data processing unit 16 may receive indications of the user input of data entered into cells of action planning interface 450 and may store the data or data based on the inputted data.

The primary row includes a cell indicating a barrier name for a barrier (i.e., a barrier name cell), a cell for a barrier definition for the barrier (i.e., a barrier definition cell), and a cell for notes for objectives regarding the barrier (i.e., an objectives cell). Data processing unit 16 may automatically output the barrier name and the barrier definition data for the barrier from barrier prioritization interface 350 in the barrier name cell for the barrier and the barrier definition cell for the barrier. The user may input into the objectives cell notes regarding the hospital's objectives for reducing the barrier. As one example, if Referral Motivation is considered a key barrier, an objective could be to conduct four training sessions in a one-year period given by subject matter experts to physicians who may see the patients with a particular indication in their daily practice but do not recognize them. Another example objective may be to partner with industry and conduct a randomized, clinical study over a 5-year period to provide clear benefit data (assuming Clinical Evidence is a barrier).

In the example of FIG. 12, the medical therapy may be an implantable medical device having leads. Furthermore, in the example of FIG. 12, the barrier name of the barrier is "clinical capacity, skill," the barrier definition is to "provide more left-sided lead training," and an objective is to collaborate with industry virtual lead placement program and CME funding." CME is an acronym for Continuing Medical Education.

Furthermore, each primary row of action planning interface 450 may include one or more secondary rows. Each of the secondary rows of a primary row corresponds to a different strategy for reducing the barrier (i.e., a barrier reduction strategy) that corresponds to the primary row. Each of the secondary rows includes a strategy cell, a Y1 cell, a Y2 cell, a Y3 cell, a Y4 cell, a Y5 cell, a total cell, an owner cell, and a notes cell. A user may input a description of a barrier reduction strategy in a strategy cell. Furthermore, the user may input data describing executional milestones and investment needs for years 1 through 5 of executing a barrier reduction strategy in the Y1, Y2, Y3, Y4, and Y5 cells. An executional milestone may be a goal that is to be achieved by a particular time in the future. In any embodiment of the first through seventh aspects of the invention, the investment needs may be denoted in thousands of dollars. Furthermore, data processing unit 16 may automatically output for display in the total cell for a secondary row, a total of the inputted investment needs for years 1 through 5 of executing a barrier reduction strategy.

A user may input (and data processing unit 16 may receive) data indicating an owner for each of the strategies corresponding to the secondary rows of action planning interface 450. The owner for a strategy may be one or more persons responsible for implementing the strategy. A user may also input notes regarding a strategy in the notes cell for the strategy.

As one example of the type of data that a user may enter (and data processing unit 16 may receive) in any embodiment of the first through seventh aspects of the invention, in action planning interface 450, the hospital may choose to prioritize three barriers for reduction. In this example, the first prioritized barrier may be a lack of referrer awareness of the hospital's ability to provide the medical therapy. In this example, the second prioritized barrier may be a lack of referrer linkages. Furthermore, in this example, the third prioritized barrier may be a lack of specialized nurses at the hospital. In this example, a user may input, as a strategy for the first prioritized barrier, "clinical decision support with patient screening tools and evidence dissemination to referrers." In this example, the user may input, as a strategy for the second prioritized barrier, "in-hospital monthly educational workshops with referrers in the community." Furthermore, in this example, the user may input, as a strategy for the third prioritized barrier, "education and specialization of nurses on the medical condition treatable by the medical therapy to screen patients in general wards."

In the example of FIG. 12, the user has entered "provide KOL proctor," "develop quarterly access to virtual system and train new implanters," and "develop CME course for team" as strategies for reducing the "clinician capacity, skill" barrier. Furthermore, in this example, the user may input, as executional milestones for the "provide KOL proctor" strategy, "find proctor," "hold 4 programs," "hold 2 programs," "hold 1 program," and "hold 1 program." In this example, the user may input, as investment needs corresponding to the above-indicated executional milestones for the "provide KOL proctor" strategy, "5,000," "200,000," "100,000," "100,000," and "10,000." In this example, the user may input, as executional milestones for the "develop quarterly access to virtual system and train new implanters" strategy, "partner with industry for virtual system access" and "complete quarterly training." In this example, the user may input, as investment needs corresponding to the above-indicated executional milestones for the "develop quarterly access to virtual system and train new implanters" strategy, "0" and "30,000." Furthermore, in this example, the user may input, as executional milestones for the "develop CME course for team" strategy, "identify off the shelf CME sources and implement" and "Continue program." In this example, the user may input, as investment needs corresponding to the above-indicated executional milestones for the "develop CME course for team" strategy, "10,000" and "1,000."

In this way, the one or more barriers may include a prioritized barrier, and data processing unit 16 may output an action planning interface (e.g., action planning interface 450) for display. Data processing unit 16 may receive indications of additional data entered in data entry fields of the action planning interface, the additional data comprising data indicating a strategy for reducing the prioritized barrier, data indicating executional milestones for implementing the strategy for reducing the prioritized barrier, and data indicating investment needs for implementing the strategy for reducing the prioritized barrier.

In any embodiment of the first through seventh aspects of the invention, the action planning interface may display a prioritization of actions. In any embodiment of the first through seventh aspects of invention, the prioritization of the actions in the action planning interface can be based on calculated correlation coefficients, as explained herein. Because, based on the calculated correlation coefficients, the system can estimate the effect of reducing a barrier on the number of times the healthcare provider will provide the therapy, the system can also determine which actions are most likely to reduce which barriers, and therefore which actions are most likely to increase the number of times the healthcare provider provides the therapy.

Figure 13:
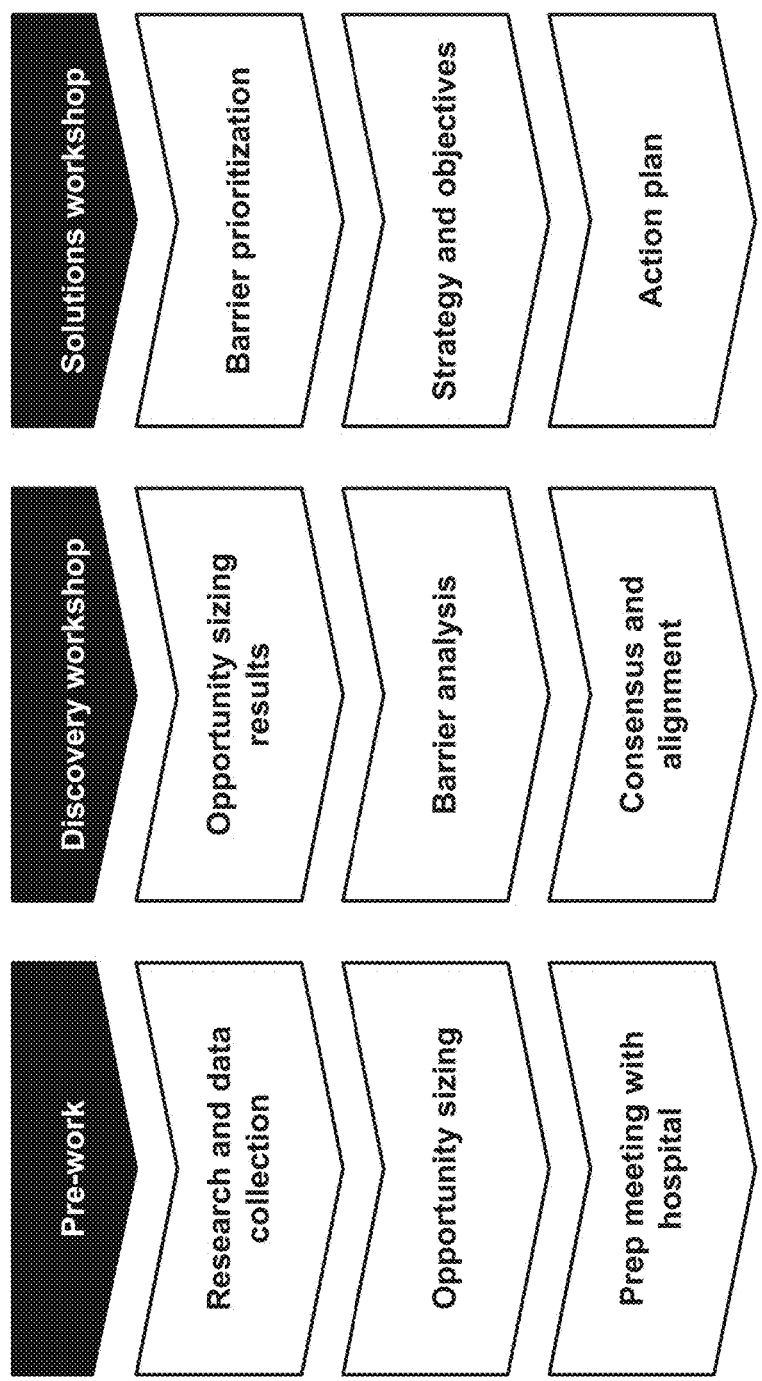
FIG. 13 is a conceptual diagram illustrating example phases of a decision-making process, in accordance with one or more techniques of this disclosure.

FIG. 13 is a conceptual diagram illustrating example phases of a decision-making process, in accordance with one or more techniques of this disclosure. In the example of FIG. 13, the decision-making process is divided into three phases: a pre-work phase, a discovery workshop phase, and a solutions workshop phase. Different phases may involve different groups of people associated with the healthcare provider. For instance, actions occurring in the pre-work phase many involve administrators of the healthcare provider. Actions occurring in the discovery workshop phase and the solutions workshop phase may include administrators, physicians, department heads, nursing staff, and/or other staff of the healthcare provider (e.g., hospital).

As shown in the example of FIG. 13, the pre-work phase may involve research and data collection, opportunity sizing, and preparation for future meetings. As part of the data collection and opportunity sizing actions, the administrator may collect and input the information into an opportunity sizing interface, such as that shown in FIGS. 4 and 5.

The discovery workshop phase may be conducted as a meeting that includes discussion of opportunity sizing results. For instance, an administrator may share, with other meeting participants, opportunity sizing diagrams and opportunity comparison diagrams generated by computing system 10 (e.g., the opportunity sizing diagrams of FIGS. 5 and 6 and the opportunity comparison diagram of FIG. 7). Furthermore, in the discovery workshop phase, a barrier analysis may be performed. As part of performing the barrier analysis, participants of the discovery workshop may discuss and provide answers to multiple-choice questions regarding specific barriers to patients accessing a medical therapy from the hospital. For instance, the participants of the discovery workshop may select answers to the multiple-choice questions discussed elsewhere in this disclosure. Furthermore, participants in the discovery workshop phase may conduct a discussion to attempt to reach a consensus regarding the desirability to reduce barriers to patients accessing the medical therapy from the hospital and that such barriers exist.

The solutions workshop phase may be conducted as a separate meeting from the discovery workshop. During the solutions workshop, participants may perform a barrier prioritization process. As part of performing the barrier prioritization process, a user may input (and computing system 10 may receive) barrier prioritization data into a barrier prioritization user interface, such as barrier prioritization interface 350 of FIG. 10. Furthermore, as part of performing the barrier prioritization process, participants may review a barrier prioritization matrix, such as barrier prioritization matrix 400 of FIG. 11, that is based on the barrier prioritization data. The barrier prioritization matrix may provide a visual way of comparing potential barriers for prioritization.

Furthermore, during the solutions workshop, participants may formulate strategies and objectives for reducing one or more prioritized barriers to patients accessing the medical therapy from the hospital. As part of formulating the strategies and objectives, a user may input (and computing system 10 may receive) descriptions of the strategies and objectives in an action planning interface, such as action planning interface 450 of FIG. 12. Moreover, during the solutions workshop, participants may produce an action plan for achieving the strategies and objectives. Producing the action plan may involve identifying executional milestones and investment needs, assigning owners to particular strategies, and so on. A user may input descriptions of such executional milestones, investment needs, owner, and other data into an action planning interface, such as action planning interface 450 of FIG. 12.

Figure 14:
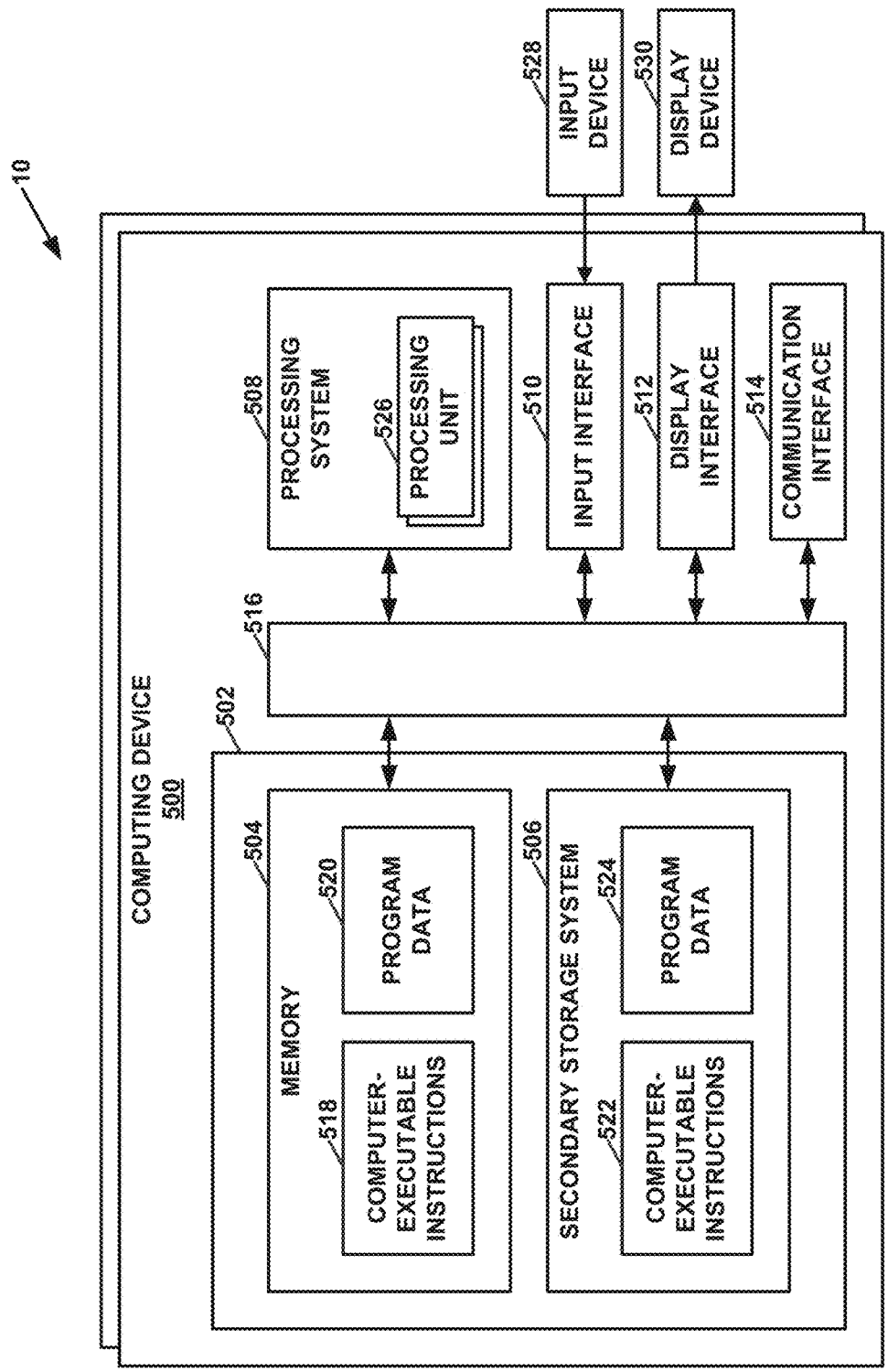
FIG. 14 is a block diagram of an example configuration of a computer system which may be configured to implement the techniques of this disclosure.

FIG. 14 is a block diagram of an example configuration of a computing system 10, which may be configured to implement the techniques of this disclosure. In the example of FIG. 14, computing system 10 comprises a computing device 500 and one or more other computing devices.

Computing device 500 may be a physical device that processes information. In the example of FIG. 14, computing device 500 comprises a data storage system 502, a memory 504, a secondary storage system 506, a processing system 508, an input interface 510, a display interface 512, a communication interface 514, and one or more communication media 516. Communication media 516 may enable data communication between processing system 508, input interface 510, display interface 512, communication interface 514, memory 504, and secondary storage system 506. Computing device 500 may include components in addition to those shown in the example of FIG. 14. Furthermore, some computing devices do not include all of the components shown in the example of FIG. 14.

A computer system-readable medium may comprise a medium from which a processing system can read data. Computer system-readable media may include computer system storage media and communications media. Computer system storage media may include physical devices that store data for subsequent retrieval. Computer system storage media are not transitory (i.e., non-transitory). For instance, computer system storage media do not exclusively comprise propagated signals. Computer system storage media may include volatile storage media and non-volatile storage media. Example types of computer system storage media may include random-access memory (RAM) units, read-only memory (ROM) devices, solid state memory devices, optical discs (e.g., compact discs, DVDs, Blu-ray discs, etc.), magnetic disk drives, electrically-erasable programmable read-only memory (EEPROM), programmable read-only memory (PROM), magnetic tape drives, magnetic disks, and other types of devices that store data for subsequent retrieval. Communication media may include media over which one device can communicate data to another device. Example types of communication media may include communication networks, communications cables, wireless communication links, communication buses, and other media over which one device is able to communicate data to another device.

Data storage system 502 may comprise a system that stores data for subsequent retrieval. In the example of FIG. 14, data storage system 502 comprises memory 504 and secondary storage system 506. Memory 504 and secondary storage system 506 may store data for later retrieval. In the example of FIG. 14, memory 504 stores computer system-executable instructions 518 and program data 520. Furthermore, in the example of FIG. 14, secondary storage system 506 stores computer system-executable instructions 522 and program data 524. Physically, memory 504 and secondary storage system 506 may each comprise one or more computer system storage media.

In the example of FIG. 14, processing system 508 is coupled to data storage system 502. Processing system 508 may read computer system-executable instructions from data storage system 502 and may execute the computer system-executable instructions. Execution of the computer system-executable instructions by processing system 508 may configure and/or cause computing device 500 to perform the actions indicated by the computer system-executable instructions. For example, execution of the computer system-executable instructions by processing system 508 can configure and/or cause computing device 500 to provide Basic Input/Output Systems (BIOS), operating systems, system programs, application programs, or may configure and/or cause computing device 500 to provide other functionality.

Processing system 508 may read the computer system-executable instructions from one or more computer system-readable media. For example, processing system 508 may read and execute computer-executable instructions 518 and 522 stored on memory 504 and secondary storage system 506.

Processing system 508 may comprise one or more processing units 526. Processing units 526 may comprise physical devices that execute computer system-executable instructions. Processing units 526 may comprise various types of physical devices that execute computer system-executable instructions. For example, one or more of processing units 526 may comprise a microprocessor, a processing core within a microprocessor, a digital signal processor, a graphics-processing unit, or another type of physical device that executes computer system-executable instructions.

Input interface 510 may enable computing device 500 to receive input from an input device 528. Input device 528 may comprise a device that receives input from a user. Input device 528 may comprise various types of devices that receive input from users. For example, input device 528 may comprise a keyboard, a touch screen, a mouse, a microphone, a keypad, a joystick, a brain-computer system interface device, or another type of device that receives input from a user. In any embodiment of the first through seventh aspects of the invention, input device 528 is integrated into a housing of computing device 500. In any embodiment of the first through seventh aspects of the invention, input device 528 is outside a housing of computing device 500. In any embodiment of the first through seventh aspects of the invention, input device 528 may receive input of quantitative data used in generating the various user interfaces described in this disclosure for facilitating a decision-making process regarding reduction of one or more barriers to patients accessing medical therapies from a healthcare provider.

Display interface 512 may enable computing device 500 to display output on a display device 530. Display device 530 may be a device that presents output. Example types of display devices include printers, monitors, touch screens, display screens, televisions, and other types of devices that display output. In any embodiment of the first through seventh aspects of the invention, display device 530 is integrated into a housing of computing device 500. In any embodiment of the first through seventh aspects of the invention, display device 530 is outside a housing of computing device 500. In any embodiment of the first through seventh aspects of the invention, display device 530 may present the different user interfaces as described above.

Communication interface 514 may enable computing device 500 to send and receive data over one or more communication media. Communication interface 514 may comprise various types of devices. For example, communication interface 514 may comprise a Network Interface Card (NIC), a wireless network adapter, a Universal Serial Bus (USB) port, or another type of device that enables computing device 500 to send and receive data over one or more communication media.

Figure 15:
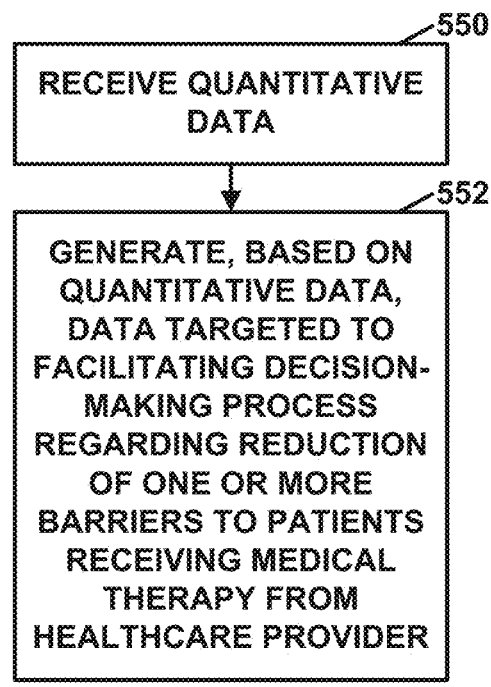
FIG. 15 is a flowchart illustrating an example process of a computing system, in accordance with one or more techniques of this disclosure.

FIG. 15 is a flowchart illustrating an example process of computing system 10, in accordance with one or more techniques of this disclosure. In the example of FIG. 15, computing system 10 may receive quantitative data (550). The quantitative data may include the data entered into the various data entries fields of the user interfaces described elsewhere in this disclosure (e.g., the opportunity sizing interface of FIGS. 4 and 5, the barrier assessment questions, barrier prioritization interface 350 of FIG. 10, action planning interface 450, etc.) Furthermore, in the example of FIG. 15, computing system 10 may generate, based on the quantitative data, data targeted to facilitating a decision-making process regarding reduction of one or more barriers to patients receiving a medical therapy from a healthcare provider (552). The generated data may include data presented in the various interfaces and diagrams described elsewhere in this disclosure (e.g., in the interfaces described in FIGS. 4-12).

Figure 16:
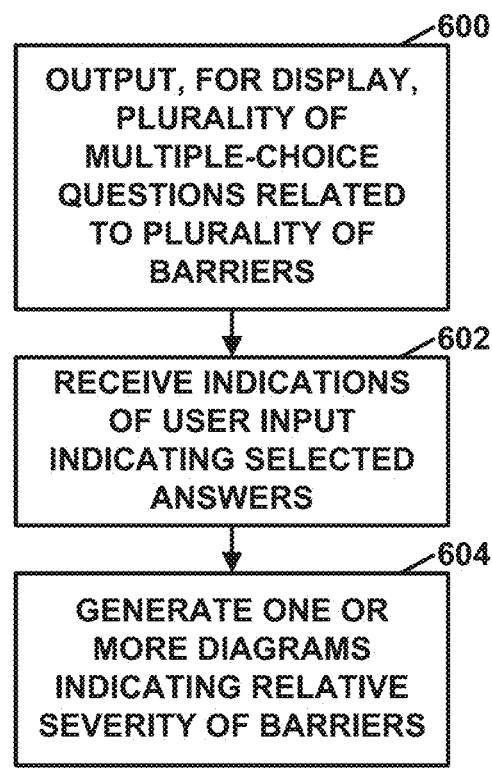
FIG. 16 is a flowchart illustrating another example process of a computing system, in accordance with one or more techniques of this disclosure.

FIG. 16 is a flowchart illustrating another example process of computing system 10, in accordance with one or more techniques of this disclosure. In the example of FIG. 16, computing system 10 may output, for display, a plurality of multiple-choice questions related to a plurality of barriers to patients receiving a medical therapy from a healthcare provider (600). The plurality of barriers may include barriers related to: clinical evidence, reimbursement, physician economics, physician capacity and training level for the medical therapy, treatment capacity, and so on. Furthermore, computing system 10 may receive indications of user input indicating selected answers to the multiple-choice questions (602). Each of the answers to the multiple-choice questions may correspond to a quantitative value. In addition, computing system 10 may generate, based on the quantitative values corresponding to the selected answers, one or more diagrams indicating relative severity of the barriers in preventing the patients from receiving the medical therapy from the healthcare provider (604).

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the one or more processors. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In any embodiment of the first through seventh aspects of the invention, an article of manufacture may comprise one or more computer system-readable storage media.

Various examples have been described. These and other examples are within the scope of the following claims.

We claim:

1. A system, comprising:
one or more processors configured to provide an initial barrier prioritization rank order of a plurality of barriers, each barrier preventing patients from receiving a medical therapy from a healthcare provider;
wherein the initial barrier prioritization rank order is an order of the barriers ranked based on a plurality of correlation coefficients calculated for each of the plurality of barriers, the correlation coefficient representing an effect of reducing the corresponding barrier on a number of times the medical therapy is provided by the healthcare provider;
the one or more processors configured to receive data indicative of the plurality of barriers preventing patients from receiving the medical therapy from the healthcare provider, wherein the data is information showing an impact or severity of the plurality of barriers; and
the one or more processors uses an initial plurality of correlation coefficients to determine subsequent barrier prioritization rank order using the initial barrier prioritization rank order based on an analysis of the received data indicative of the plurality of barriers preventing patients from receiving medical therapy from healthcare provider,
the one or more processors configured to derive an annual adoption rate equation, wherein the annual adoption rate equation is defined as:

$$N \div (Y \times (1+P))$$

wherein N is the number of times the healthcare provider provides the therapy, Y is the number of years, and P is the penetration of incidence;
the one or more processors configured to constantly update the annual adoption rate equation and the plurality of correlation coefficients by performing statistical calculations for each time new data concerning an opportunity size and the number of times the medical therapy is provided by the healthcare provider are entered,
wherein the one or more processors are configured to provide an action plan of one or more actions based on the data indicative of the plurality of barriers and the subsequent barrier prioritization rank order preventing patients from receiving the medical therapy, the action plan comprising the steps of:
determining at least one strategy for addressing the plurality of barriers and/or increasing the annual adoption rate, wherein the at least one strategy is selected from the group consisting of: clinical decision support with patient screening tools and evidence dissemination to referrers, in-hospital monthly educational workshops with referrers in the community, education and specialization of nurses on the medical condition treatable by the medical therapy to screen patients in general wards; and combinations thereof;
identifying one or more executional milestones for the one or more strategies, and identifying one or more investment needs to execute the one or more strategies;

wherein the one or more processors are configured to determine a barrier prioritization matrix based on an indication of priority of the barriers listed in the subsequent barrier prioritization rank order, wherein the barrier prioritization matrix correlates to an impact on success and an ability to impact for each one of the barriers, wherein the impact on success is a function of the ability to impact, and wherein the impact on success corresponds to an effect on a number of times the healthcare provider provides the medical therapy due to reduction of the plurality of barriers and the ability to impact corresponds to an ability of the healthcare provider to reduce the plurality of barriers.

2. The system of claim 1, wherein the correlation coefficient is calculated for each barrier with respect to the annual adoption rate equation.

3. The system of claim 1, wherein the data indicative of the plurality of barriers preventing patients from receiving medical therapy from the healthcare provider is obtained from a response to a multiple choice question, wherein the response is converted into a quantitative value and used to determine the subsequent barrier prioritization rank order.

4. The system of claim 1, wherein the plurality of barriers is selected from the group consisting of: Clinical Evidence, Practice Guidelines, Complication Rates, Readmissions, Clinical Outcomes Measurement, Reimbursement, Budget Availability, Cost of Care for Procedure, Cost of Care Follow-up, Physician Economics, Infrastructure Investment, Financial Metrics, Diagnostic Capacity, Patient Screening Selection, Treatment Capacity, Clinician Capacity in Skill, Procedure Standardization, Length of Stay, Follow-up Capacity, Follow-up Care Process, Patient Concentration, Referrer Motivation, Community Referral Links, Interdepartment Patient Pathways, Prescriber Motivation, Standardization of Care, Hospital Reputation, Patient Education and Resources, Patient Experience Measurement, and Patient Satisfaction.

5. The system of claim 4, wherein the barriers are grouped in categories of any one or more of Clinical Excellence, Hospital Economics, Capacity and Efficiency, Patient Pathways, and Patient Experience.

6. The system of claim 1, wherein the one or more processors provide any one of the initial barrier prioritization rank order, the subsequent barrier prioritization rank order, or the action plan.

7. The system of claim 1, further comprising a graphical user interface, wherein the graphical user interface is configured to display one or more multiple choice questions regarding the plurality of barriers, and wherein the data indicative of the plurality of barriers to patients receiving the medical therapy from the healthcare provider is obtained at least in part from one or more answers to the multiple choice questions.

8. The system of claim 1, wherein at least part of the data indicative of the plurality of barriers to patients receiving the medical therapy from healthcare provider is obtained electronically by the system.

9. The system of claim 1, wherein the system is further configured to output an action planning interface for display; wherein the action planning interface displays a prioritization of actions; wherein the prioritization of actions is based on estimated effect of reducing a barrier by an action, the estimated effect of reducing the barrier corresponding to a likely change on the number of times the healthcare provider provides the medical therapy, and wherein the action planning interface receives and stores a user's input.

10. A method, comprising:
selecting a plurality of barriers from the group consisting of:
Clinical Evidence, Practice Guidelines, Complication Rates, Readmissions, Clinical Outcomes Measurement, Reimbursement, Budget Availability, Cost of Care for Procedure, Cost of Care Follow-up, Physician Economics, Infrastructure Investment, Financial Metrics, Diagnostic Capacity, Patient Screening Selection, Treatment Capacity, Clinician Capacity in Skill, Procedure Standardization, Length of Stay, Follow-up Capacity, Follow-up Care Process, Patient Concentration, Referrer Motivation, Community Referral Links, Interdepartment Patient Pathways, Prescriber Motivation, Standardization of Care, Hospital Reputation, Patient Education and Resources, Patient Experience Measurement, and Patient Satisfaction;

grouping the barriers in the categories of any one or more of Clinical Excellence, Hospital Economics, Capacity and Efficiency, Patient Pathways, and Patient Experience;

determining by one or more processors an initial barrier prioritization rank order of the plurality of barriers preventing patients from receiving a medical therapy from a healthcare provider, wherein the initial barrier prioritization rank order is an order of the barriers ranked based on a plurality of correlation coefficients calculated for each of the barriers and wherein the correlation coefficient represents an effect of reducing the barrier on a number of times the medical therapy is provided by the healthcare provider;

receiving data indicative of the plurality of barriers preventing patients from receiving the medical therapy from the healthcare provider wherein the data is information showing impact or severity of the plurality barriers;

calculating a relative severity between each one of the plurality of barriers using a weight for each of the barriers, wherein the weight is based on the correlation coefficient for each of the barriers;

determining a subsequent barrier prioritization rank order using the initial barrier prioritization rank order based on an analysis of the received data indicative of the plurality of barriers preventing patients from receiving medical therapy from the healthcare provider;

deriving an annual adoption rate equation, wherein the annual adoption rate equation is defined as:

$$N \div (Y \times (1+P))$$

wherein N is the number of times the healthcare provider provides the therapy, Y is the number of years, and P is the penetration of incidence;

constantly updating the annual adoption rate equation and the plurality of correlation coefficients by performing statistical calculations for each time new data concerning an opportunity size and the number of times the medical therapy is provided by the healthcare provider are entered;

determining an action plan of one or more actions reducing the plurality of barriers and/or increasing the annual adoption rate based on the calculated correlation coefficient and the subsequent barrier prioritization rank order, the action plan comprising the steps of:

determining at least one strategy for addressing the plurality of barriers, wherein the at least one strategy is selected from the group consisting of: clinical decision support with patient screening tools and evidence dissemination to referrers, in-hospital monthly educational workshops with referrers in the community, education and specialization of nurses on the medical condition treatable by the medical therapy to screen patients in general wards; and combinations thereof;

identifying one or more executional milestones for the one or more strategies, and identifying one or more investment needs to execute the one or more strategies; and displaying on a graphical user interface a barrier prioritization matrix based on an indication of priority of the barriers listed in the subsequent barrier prioritization rank order, wherein the barrier prioritization matrix correlates to an impact on success and an ability to impact for each one of the barriers, wherein the impact on success is a function of the ability to impact, and wherein the impact on success corresponds to an effect on a number of times the healthcare provider provides the medical therapy due to reduction of the plurality of barriers and the ability to impact corresponds to an ability of the healthcare provider to reduce the plurality of barriers.

11. The method of claim 10, wherein the data indicative of the plurality of barriers preventing patients from receiving the medical therapy from the healthcare provider is obtained from a response to a multiple choice question, wherein the response is converted to a quantitative value and used to determine the subsequent barrier prioritization rank order.

12. The method of claim 10, further comprising the step of: indicating priority for the plurality of barriers in the subsequent barrier prioritization rank order.

13. The method of claim 10, further comprising the step of: estimating an ability of the health care provider to reduce the plurality of the barriers.

14. The method of claim 13, wherein estimating the ability of the health care provider to reduce the plurality of the barriers is based at least in part on previous success in reducing the barriers in one or more other therapies by the healthcare provider.

15. The method of claim 10, wherein the one or more actions are prioritized based on an estimated effect of taking an action on the number of times the healthcare provider will provide the medical therapy in the future.

16. The method of claim 10, further comprising the step of: displaying any one of the initial barrier prioritization rank order, the subsequent barrier prioritization rank order, or the action plan.

17. The system of claim 1, wherein the correlation coefficient represents an effect of a change in a barrier score for each of the barriers on the number of times the healthcare provider provides the medical therapy, the barrier score representing sums of values assigned to each of answered questions regarding each of the barriers.

18. The system of claim 17, wherein the correlation coefficient of one of the barriers is updated based on the barrier scores for other ones of the barriers.

19. The system of claim 1, wherein at least part of the number of times the medical therapy is provided by the healthcare provider is updated automatically by the system based on an electronic signal indicating the medical therapy is performed by the healthcare provider.

20. The system of claim 1, further comprising the step of reducing at least one of the barriers.

21. The method of claim 10,
wherein the Clinical Excellence category consists of Clinical Evidence, Practice Guidelines, Complication Rates, Readmissions, and Clinical Outcomes Measurement,
the Hospital Economics category consists of Reimbursement, Budget Availability, Cost of Care for Procedure, Cost of Care Follow-up, Physician Economics, Infrastructure Investment, and Financial Metrics,
the Capacity and Efficiency category consists of Diagnostic Capacity, Patient Screening Selection, Treatment Capacity, Clinician Capacity in Skill, Procedure Standardization, Length of Stay, Follow-up Capacity, and Follow-up Care Process,
the Patient Pathways category consists of Patient Concentration, Referrer Motivation, Community Referral Links, Interdepartment Patient Pathways, Prescriber Motivation, and Standardization of Care, and
the Patient Experience category consists of Hospital Reputation, Patient Education and Resources, Patient Experience Measurement, and Patient Satisfaction.

22. The system of claim 1, wherein the one or more processors are configured to periodically update the plurality of correlation coefficients at least once a week, at least once a month, or at least once a year.

* * * * *